US008263756B2

(12) United States Patent
Takahara et al.

(10) Patent No.: US 8,263,756 B2
(45) Date of Patent: Sep. 11, 2012

(54) METHOD OF GENE TRANSFER VIA VASCULAR SYSTEM OR URETER

(75) Inventors: Shiro Takahara, Osaka (JP); Enyu Imai, Hyogo (JP); Yoshitaka Isaka, Osaka (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 10/474,142

(22) PCT Filed: Mar. 22, 2002

(86) PCT No.: PCT/JP02/02770
§ 371 (c)(1),
(2), (4) Date: Apr. 23, 2004

(87) PCT Pub. No.: WO02/083185
PCT Pub. Date: Oct. 24, 2002

(65) Prior Publication Data
US 2004/0175370 A1 Sep. 9, 2004

(30) Foreign Application Priority Data
Apr. 6, 2001 (JP) .................. 2001-109051

(51) Int. Cl.
*C07H 21/02* (2006.01)
*C07H 21/04* (2006.01)
(52) U.S. Cl. ..................................... 536/23.1
(58) Field of Classification Search ............. 536/23.1; 514/44
See application file for complete search history.

(56) References Cited

U.S. PATENT DOCUMENTS
5,869,230 A 2/1999 Sukhatme

FOREIGN PATENT DOCUMENTS

| AU | 9653241 | 10/1996 |
|---|---|---|
| AU | 200012038 | 5/2000 |
| EP | 0462549 | 12/1991 |
| EP | 817861 | 1/1998 |
| FR | 2717569 | 8/1995 |
| JP | 4-49246 | 2/1992 |
| JP | 11-503123 | 3/1999 |
| JP | 11103858 | * 4/1999 |
| WO | WO 96/30535 | 10/1996 |
| WO | WO 00/22095 | 4/2000 |
| WO | WO 00/62855 | * 10/2000 |
| WO | WO 00/66179 | 11/2000 |
| WO | WO 02/00264 | 1/2002 |

OTHER PUBLICATIONS

Jung et al (2001, PNAS, 98:2676-2681).*
Nishi et al. (1996, Cancer Research, 56: 1050-1055).*
Lu et al. (1999, Cancer Gene Therapy, 6: 64-72).*
Leopold et al., 1996, Genetic Analysis: Biomolecular Engineering, 12: 197-200.*
Lowenstein and Castro, 2004, Current Opinion in Pharmacology, 4: 91-97.*
Yoo et al., 1999, The Journal of Urology, 162: 1115-1118.*
Hammer et al., 1986, J. of Anim. Sci., 63: 269-278.*
Samstein and Platt, 2001, J. Am Soc. Nephrol., 12: 182-193.*
Cascalho et al., 2004, J. Am. Soc. Nephrol., 15: 1106-112.*
van Oekelen, et al., 2003, Brain Research Reviews, 42: 123-142.*
Hammer et al. 1990, Cell, 6: 1099-1112.*
Cowan et al. 2003, Xenotransplantation, 10: 223-231.*
Racay, 2002, Bratisl Lek Listy, 103: 121-126.*
Vicat et al., 2000, Human Gene Therapy, 11: 909-916.*
Gage, 1998, Nature, 392 Supp.: 18-24.*
Amiel et al., 2000, World J. Urol., 18: 71-79.*
Lai et al., 1998, J. Clin. Invest. 101: 1320-1325.*
Parpala-Sparman et al., 1999, Urol. Res. 27: 97-102.*
Tekle et al., 1991, PNAS, USA, 88: 4230-4234.*
Yo et al., 1998, Kidney International, 54: 1128-1138.*
Quaggin et al., 1997, The Journal of Clinical Investigation, 99: 718-724.*
Hanze et al., 1998, Biotechnology Techniques, 12: 159-163.*
Kaneda et al., 1999, Molecular Medicine Today, 5: 298-303.*
Tsujie et al. 2001, Kidney International, 59: 1390-1396.*
Nishi et al., 1996, Cancer Research, 56: 1050-1055.*
Berg et al., 2004, Journal of Histochemical and Cytochemistry, 52: 1101-1106.*
Yim et al., 2009, Korean Journal of Pediatrics, 52: 944-952.*
Haas et al., 2003, J. Am Soc. Nephrol., 14: 2288-2296.*
Heikkila et al., 1996, Gene Therapy, 3: 21-27.*
Zhang et al., 1997, Bioelectrochemistry and Bioenergetics, 42: 283-292.*
Harrison et al., 1998, FEBS Letters, 435: 1-5.*
Zhu et al., 1996, Gene Therapy, 3: 298-304.*
Isaka Y. et al, "Gene Therapy Aimed at Long-Term Survival of Transplanted Kidneys", The Japanese Society of Nephrology, p. W-5-4 (2001).
Imai N. et al., "Potential application of gene therapy to the therapy of renal diseases", Kidney and Dialysis, vol. 49(6), pp. 1021-1024 (2000).
Imai N. et al., "Gene therapy and tissue engineering in nephrology and renal transplantation", Nihon Rinsho, vol. 59(1), pp. 65-71 (2001).
Imai N. et al., "Perspective in gene therapy for renal diseases", Journal of Osaka Society for Dialysis Therapy, vol. 18(2), pp. 193-197 (2000).
Imai N. et al., "Jin eno Idenshi Donyu to Idenshi Chiryo", Igaku no Ayumi, vol. 193(1), pp. 87-90 (2000).

(Continued)

*Primary Examiner* — Joanne Hama
(74) *Attorney, Agent, or Firm* — Fish & Richardson P.C.

(57) ABSTRACT

The present invention provides a method for gene transfer through the vascular system or a ureter. In a preferable embodiment of this invention, an aqueous solution containing an expression vector comprising a desired gene is injected through the vascular system or a ureter of a desired organ to introduce the gene into the injected area. Specifically, the method of the present invention is effective for ex vivo gene therapy wherein the hepatocyte growth factor (HGF) gene is introduced by electroporation into a kidney to be transplanted. According to the present invention, the HGF functions continuously on the kidney to be transplanted, and the HGF within the treated area does not affect other organs of the body. Thus, the method of the present invention is a safe and effective treatment for maintaining the survival of transplanted kidneys.

42 Claims, 17 Drawing Sheets

OTHER PUBLICATIONS

Tsujie M. et al., "Electroporation Ho o Mochiita Jin Shikyutai eno Idenshi Donyu Ho no Kaihatsu", vol. 42(3), The Japanese Society of Nephrology, p. 198 (2000).

Nakamura H. et al., "Electroporation Ho o Mochiita Egr-1 DNA Enzyme Donyu ni yoru Jinkanshitsu Shogai Shinten no Yokusei", The Japanese Society of Nephrology, p. O-142 (2001).

Imai E. et al., "Gene therapy for kidney disease", Expert Opin. Investig. Drugs, vol. 9(5), pp. 1029-1039 (2000).

Tsujie M. et al., "Gene transfer targeting interstitial fibroblasts by the artificial viral envelope-type hemagglutinating virus of Japan liposome method", Kidney Int., vol. 57(5), pp. 1973-1980 (2000).

Mizuno S. et al., "Ishoko Igaku ni okeru HGF no Yakuwari", Igaku no Ayumi, vol. 196(13), pp. 905-912 (2001).

Azuma H. et al., "Hepatocyte Growth Factor (HGF) no Mansei Kyozetsu Hanno (Rat Ishoku Jin) ni taisuru Chiryo Koka", The Japanese Journal of Urology, vol. 90(2), p. 150 (1999).

Azuma H. et al., "Hepatocyte Growth Factor (HGF) no Mansei Kyozetsu Hanno (Rat Ishoku Jin) ni taisuru Chiryo Koka", The Japanese Journal of Urology, vol. 92(2), p. 184 (2001).

Isaka Y. et al., "Ishoku Jin no Choki Seichaku o Mezashita Idenshi Chiryo", The Japanese Journal of Nephrology, vol. 43(3), p. 164 (2001).

Maruyama H. et al., "Kidney-Targeted Naked DNA Transfer by Retrograde Vein Injection in Rats", Human Gene Therapy, vol. 13(3), pp. 455-468 (2002).

Dai C. et al., "Single injection of naked plasmid encoding hepatocyte growth factor prevents cell death and ameliorates acute renal failure in mice", J. Am. Soc. Nephrol., vol. 13(2) pp. 411-422 (2002).

Nakamura H. et al., "Electroporation Ho o Mochiita Egr-1 DNA Enzyme Donyu ni yoru Jinkansitsu Shogai Shinten no Yokusei", The Japanese Journal of Nephrology, vol. 43(3), p. 189 (2001).

Tsujie M. et al., "Electroporation-Mediated Gene Transfer that Targets Glomeruli", J. Am. Soc. Nephrol, vol. 12(5), pp. 949-954 (2001).

Imai E. et al., "Gene electrotransfer: Potential for gene therapy of renal diseases", Kidney Int., vol. 61(1 Suppl), pp. 37-41 (2002).

David E. Larson, M.D., Editor-in-Chief, "The Kidneys and Urinary Tract", p. 911 from the Mayo Clinic Family Health Book, William Morrow and Company, Inc., N.Y., 1990.

Moullier et al., "Adenoviral-mediated gene transfer to renal tubular cells in vivo", Kidney Int. vol. 45, p. 1220 (1994).

Santiago et al., "New DNA enzyme targeting Egr-1 mRNA inhibits vascular smooth muscle proliferation and regrowth after injury", Nature Medicine, vol. 5, pp. 1264-1269 (1991).

Lefesvre et al., "A Comparison of Efficacy and Toxicity Between Electroporation and Adenoviral Gene Transfer," *BMC Molecular Biology*, 3(12):1-13 (2002).

Terada et al., "Gene Transfer of Smad7 Using Electroporation of Adenovirus Prevents Renal Fibrosis in Post-Obstructed Kidney," *Kidney International*, 61(Symposium 1):S94-S98 (2002).

Mazéres et al., "Non invasive contact electrodes for in vivo localized cutaneous electropulsation and associated drug and nucleic acid delivery," Journal of Controlled Release, vol. 134, pp. 125-131 (2009).

Van der Wouden et al., "Approaches and methods in gene therapy for kidney disease," Journal of Pharmacological and Toxicological Methods, vol. 50, pp. 13-24 (2004).

\* cited by examiner

METHOD OF GENE TRANSFER VIA VASCULAR SYSTEM OR URETER

This application is a U.S. National Phase application that claims priority from PCT/JP02/02770, filed Mar. 22, 2002, which claims priority from Japanese application no. 2001-109051, filed Apr. 6, 2001. The contents of those applications are incorporated by reference herein.

TECHNICAL FIELD

The present invention relates to a method of gene transfer through the vascular system or via a ureter. It also relates to a method for suppressing the rejection of transplanted organs using the method of gene transfer, and a method for promoting long-term survival of transplanted organs.

BACKGROUND ART

Hepatocyte growth factor (HGF) was discovered as a potent growth factor for mature hepatocytes. A gene encoding the HGF has been cloned and its amino acid sequence has also been revealed (Biochem. Biophys. Res. Com., 122:1450 (1984); Proc. Natl. Acad. Sci. USA, 83:6489, (1986); FEBS Lett., 224:311 (1987); Nature, 342:440 (1989); Proc. Natl. Acad. Sci. USA, 87:3200 (1990)). Through diverse studies, it has been revealed that HGF not only functions as a liver regenerating factor in the repair and regeneration of hepatopathy, but it also possesses various pharmacological effects. Therefore, HGF is expected to serve as a therapeutic agent for renal diseases as well as hepatopathy. In fact, intraperitoneal administration of HGF is shown to exhibit a therapeutic effect for renal fibrosis through the suppression of transforming growth factor-$\beta$ (TGF-$\beta$), a potent fibrogenic factor in mice that spontaneously develop nephrosis (Kidney Int., 57:937 (2000)).

Currently, most important issue in kidney transplantation is abolition of renal function (renal death) due to chronic rejection. It has been demonstrated that such chronic rejection is induced by damage such as ischemia, caused at the time of transplantation (Transplantation, 64:190 (1997)). In Japan, for cadaver-donor kidney transplantation, kidneys are removed after cardiac arrest. This results in prolonged ischemia, leading to chronic rejection and poor long-term prognosis of renal functions. On the other hand, in the case of living donor kidney transplantation, since more than half of all donors are 60 years or older, these kidneys have less reserve force which leads to chronic rejection.

HGF is expected to serve as a novel therapeutic agent aiming to arrest abolition of renal function due to chronic rejection and improving the survival rate of transplanted kidney. About half of all transplanted kidneys are abolished after 32 weeks in Lewis rats transplanted with kidneys from Fisher rats, a rat model for chronic rejection of transplanted kidney. However, when HGF was intravenously administered daily for 4 weeks after transplantation to the model rats, all of the transplanted kidneys survived up to 32 weeks without additional HGF administration. Namely, HGF is known to have the action of protecting transplanted kidneys (Transplant Proc., 31:854 (1999)). This report is significant in showing that suppression of initial damages after transplantation by HGF improves the survival rate of transplanted kidneys without further treatment.

In general, proteins are administered by systemic routes such as intravenous injection. However, HGF protein has a short half-life in blood. Moreover, when administered systemically, the diverse pharmacological actions of HGF are suspected to cause not a little influence on other organs. Therefore, the most effective strategy for reacting HGF on kidney may be methods wherein HGF can be locally and at the same time continuously reacted on the kidney. One way that could be considered to solve this problem would be to introduce an HGF gene only into the kidney to continuously and locally react HGF on the kidney. Since HGF is quickly metabolized in the liver as compared to other methods wherein the HGF gene is introduced into other tissues (such as muscle), and reacting HGF protein produced therein on the kidney, this method is considered advantageous in that: (1) only a little amount of the HGF gene is required for introduction; and (2) the influence on other organs can be reduced. In addition, gene transfer has merit in that it does not require multiple steps for purification, generally as needed for protein drugs. Although continuous injection of protein drugs has merit in that a constant concentration can be maintained in blood, it requires the attachment of a catheter for a long term, which involves results in complex manipulation and risk of infection as well as restraint on patient's movement.

Several methods have been reported for gene transfer targeting kidney, including the method that utilizes the HVJ-liposome method for the injection of a gene through the renal artery as reported by the present inventors (J. Clin. Invest., 92:2597 (1993); Kidney Int., 50:148 (1996)) and the kidney perfusion method utilizing adenovirus vectors (Gene Ther., 3:21 (1996)). However, the safety issue remains to be solved for these methods due to their use of virus vectors for gene transfer. On the other hand, while electroporation has been conventionally used as an in vitro gene transfer method, recently, its use as an effective method for in vivo gene transfer has been reported (Nat. Biotechnol., 16:867 (1998)). However, according to this previously reported method, genes are locally injected into a muscle or a tumor and electric stimuli is applied near the injected site with needle-type electrodes. However, this method has certain disadvantages, such as tissue damage. In addition, gene expression is limited to the injected site and thus it is impossible to express the desired gene in the whole of the transplanted kidney. On the other hand, a gene therapy method utilizing HGF wherein the HGF gene is introduced into a muscle of a rat liver cirrhosis model using HVJ liposome has been reported to exert a therapeutic effect on liver cirrhosis (Nat. Med., 5:226 (1999)). This method was also reported to show a therapeutic effect on a balloon injury model (Gene Ther., 7:1664 (2000)). However, the introduction of an HGF gene into a transplanted kidney to examine the survival rate has not been reported nor is there any report of the effectiveness of ex vivo gene transfer via electroporation.

DISCLOSURE OF THE INVENTION

The present invention relates to a method for ex vivo gene transfer through a vascular system or a ureter. In a particularly preferable embodiment, the present invention provides a method for introducing and expressing, by electroporation, a desired gene in the whole organ used for organ transplantation. In particular, an ex vivo HGF gene therapy that utilizes electroporation aiming to protect the transplanted kidney is provided. According to the ex vivo HGF gene therapy method utilizing electroporation of the present invention, the gene is introduced only into the transplanted kidney. Namely, the method enables continuous reaction of HGF on the targeted local site, the kidney. Thus, the method is effective in reducing adverse effects compared to systemic administrations such as intravenous injection. In addition, the method of the present invention is safe because it does not require the use of a virus vector, and advantageous in terms of cost compared to administrations of protein drugs.

Because of intensive studies to resolve the above issues, the present inventors have succeeded in introducing a desired gene into an extirpated kidney by filling the renal artery and/or vein, or the ureter of the kidney with a solution containing the gene. Specifically, the inventors revealed that filling the renal artery and/or vein, or the ureter of the extirpated kidney with a solution containing a desired gene, and conducting electroporation on the whole kidney result in introduction of the gene into all glomerulus and interstitial cells with high efficiency. Thus, according to the present method a desired gene is safely and effectively introduced evenly into the glomerulus and interstitial cells.

Rejection of a transplanted kidney is effectively suppressed by introducing a gene encoding a protein having organ damage suppressing function, such as HGF gene, into an extirpated kidney and subsequently transplanting this kidney that had received gene transfer according to the present method. The ex vivo gene transfer method of the present invention has several advantages over in vivo gene transfer wherein a gene is directly introduced into the kidney. One advantage of the present method is that it enables ex vivo introduction of a gene after removing a kidney for transplantation that prevents gene transfer in to other organs. As a second advantage, the influence of electric shock on humans (burn or muscle contraction) caused by the electric pulses used for electroporation can be avoided. The third advantage is that the procedure can be performed during transplantation, and thus no complicated manipulations, such as puncture into renal artery and insertion of cannula, are required. In addition, transplantation that uses the method of the present invention is applicable for xenogeneic transplantation of pig kidneys to humans.

Furthermore, the gene transfer method of the present invention may be used for introducing a protein undesirable for a target organ. For example, a DNA enzyme against a protein that causes fibrosis via the suppression of cell proliferation in the organ can be introduced according to the present method.

Thus, the present invention relates to a method for gene transfer through a vascular system or a ureter. More specifically, it provides:

(1) a method for introducing a desired gene into an injection area through a vascular system or a ureter of a desired organ, said method comprising the steps of injecting an aqueous solution containing an expression vector comprising the desired gene into the vascular system or the ureter of the target organ, and introducing the expression vector into the injection area;

(2) the method according to (1), wherein the expression vector is introduced into the injection area by electroporation;

(3) the method according to (1) or (2), wherein the injection area is in proximity to a blood vessel, interstitial area or surrounding area of epithelial cells;

(4) the method according to (1) or (2), wherein the injection area comprises vascular endothelial cells, vascular smooth muscle cells and/or interstitial cells;

(5) the method according to any one of (1) to (4), wherein the target organ is kidney;

(6) a method for suppressing organ rejection following transplantation, comprising the steps of:

(a) injecting an aqueous solution containing an expression vector comprising a gene encoding a protein having organ damage suppressing function into a vascular system or a ureter of a donor organ to be transplanted, and introducing the expression vector into an injection area; and (b) transplanting the organ into a recipient;

(7) a method for achieving long-term survival of a transplanted organ, comprising the steps of:

(a) injecting an aqueous solution containing an expression vector comprising a gene encoding a protein having organ damage suppressing function into a vascular system or a ureter of a donor organ to be transplanted, and introducing the expression vector into an injection area; and (b) transplanting the organ into a recipient;

(8) the method according to (6) or (7), wherein the expression vector is introduced into the injection area by electroporation in the step (a);

(9) the method according to any one of (6) to (8), wherein the organ to be transplanted is kidney;

(10) the method according to any one of (6) to (9), wherein the protein having organ damage suppressing function is HGF;

(11) a pharmaceutical composition for suppressing organ rejection following transplantation according to the method of (6), said composition containing a vector comprising a gene encoding HGF as an active ingredient;

(12) a pharmaceutical composition for achieving long-term survival of a transplanted organ according to the method of (7), said composition containing a vector comprising a gene encoding HGF as an active ingredient;

(13) the pharmaceutical composition according to (11) or (12), wherein the expression vector is introduced into the injection area by electroporation in the step (a) of (6) or (7);

(14) the pharmaceutical composition according to any one of (11) to (13), wherein the organ is kidney;

(15) a kit comprising the pharmaceutical composition according to any one of (11) to (14); and

(16) the kit according to (15), further containing an instruction describing the method of introducing a vector comprising the gene encoding HGF into a kidney to be transplanted.

Any desired gene may be used as a gene that is introduced into an extirpated organ in the present invention as long as it can be expressed within cells that comprise the organ, but preferably, the gene is operably linked to a promoter and/or enhancer that function in the cells. Particularly preferable are the pACT vector carrying the actin promoter, and the pCAGGS vector carrying the cytomegalovirus enhancer and the actin promoter. Alternatively, an adequate promoter for cell specific expression may be incorporated into the pBluescript vector for use in the present invention. In order to extend the gene expression period, a vector carrying the EBNA-1 gene or the oriP sequence of Epstein-Barr virus (EB virus) may be used. The gene to be introduced may be a cDNA or genomic DNA encoding a desired protein. Furthermore, it may be a nucleic acid encoding ribozyme, DNA enzyme, antisense nucleotide, etc. A transgene is preferably integrated into a vector carrying a viral latent infection machinery. Specifically, the combination of the EBNA-1 gene and the oriP sequence was revealed to accomplish significantly higher gene expression than individual uses thereof. Transgenes that can be used in the organ transplantation include genes encoding molecules suppressing or repairing tissue damage caused by transplantation, for example, molecules involved in the suppression of fibrosis, suppression of apoptosis or immunosuppression. Herein, a protein having the function of suppressing or repairing tissue damage due to transplantation is referred to as a "protein having organ damage suppressing function". Specifically, HGF may be preferably used for kidney transplantation.

Any sterilized aqueous solution may be used as a solution containing a desired gene of the present invention. The solution is preferably an aqueous solution which osmotic pressure is adjusted to a physiological condition, such as physiological saline. Alternatively, various buffers may also be used including phosphate buffer and citric acid buffer. For instance, the solution may be prepared by dissolving the desired gene in sterilized physiological saline, re-sterilizing by filter and then filling the solution in a sterile vessel.

A gene is injected through the vascular system (arteries and veins) or a ureter of a desired tissue organ. A solution comprising a desired gene is injected into the artery, vein and/or ureter governing the target organ, and then, preferably by performing electroporation as described below, the gene may be introduced into the whole injection area. The injection area includes areas in proximity to a blood vessel, interstitial areas and/or surrounding areas of epithelial cells. For example, the area may comprise vascular endothelial cells, vascular smooth muscle cells and/or interstitial cells. The method of the present invention enables to introduce a desired gene into these cells.

In particular, the present invention revealed that nucleic acids injected through the renal artery is specifically introduced into mesangial cells of the kidney. Thus, the present invention provides a method for introducing a desired gene into mesangial cells, comprising the steps of injecting an aqueous solution containing an expression vector comprising the desired gene into the renal artery, and introducing the expression vector into an injection area. The use of electroporation allows efficient introduction of the expression vector.

The method of the present invention may be used for xenogeneic transplantation as well as allotransplantation of organs. The organs for which the method of the present invention can be applied are not limited as long as an artery, vein or ureter governing the organ is defined, and include organs such as kidney, liver, spleen, heart and lung. The method is preferably used for kidneys. Although a gene may be introduced into an organ before its removal, it is preferable to introduce the desired gene ex vivo after the removal. When a desired gene is introduced into an organ before its removal, a solution containing the gene may be injected through the artery, vein and/or ureter to fill the organ with the gene, and then the organ may be fixed with forceps-type electrodes for electroporation. Alternatively, for introducing a desired gene into an organ after its removal, a catheter may be inserted into an artery, vein and/or ureter of the extirpated organ to fill the organ with a solution containing the gene, and then the organ may be held between electrodes for ex vivo electroporation. In the latter case, the electroporation may be performed under a condition wherein the organ is immersed in a bathtub-type electrode filled with an appropriate solution.

"Electroporation" may be used as a method for gene transfer. Devices for electroporation are commercially available, and any of these can be appropriately used. Preferably, square electroporator CUY21 (Tokiwa Science), electrosquareporator T820 (BTX Inc.), and equivalents thereof may be used.

The method of the present invention may be performed both in vivo and in vitro. For example, it may be performed in vitro in humans or other mammals, and in vivo in non-human mammals.

When electroporation was performed using forceps-type electrodes, the expression level of transgene increased in proportion to the rise of the voltage within the range of 25 V to 100 V. In order to avoid burning due to high voltage, the voltage is preferably 20 to 100 V, more preferably 40 to 90 V, and most preferably 60 to 75 V. The voltage is preferably applied square shaped for 100 milliseconds, for example, multiple times with intervals of 900 milliseconds. Use of a bathtub-type electrode for electroporation enables introduction of a gene into the whole organ. The present invention provides a method for introducing a desired gene through the vascular system or ureter into the whole desired organ, which method comprises the steps of injecting an aqueous solution containing an expression vector comprising the desired gene into the vascular system or the ureter of the target organ, and introducing the expression vector into the whole organ by applying electric stimuli to the whole organ by electroporation. When the bathtub-type electrode is used, the voltage is preferably adjusted to 30 to 50 V.

The method for gene transfer of the present invention particularly shows an excellent effect to continuously express a gene for a long period following the introduction of the gene into an organ. The present invention provides a method for expressing a desired gene in an organ for a long term, which method comprises the steps of injecting an aqueous solution containing an expression vector comprising the desired gene into the vascular system or a ureter of the target organ, and introducing the expression vector into an injection area. According to the method, the gene is introduced through the injected vascular system or the ureter into, for example, an area in proximity to a blood vessel, an interstitial region and/or a surrounding area of epithelial cells. The expression vector may be preferably introduced into the injection area by electroporation. Electroporation may be performed, for example, using forceps-type electrodes or a bathtub-type electrode. The method of the present invention is particularly suitable for ex vivo gene transfer, in which a vector is preferably introduced into an organ by electroporation using a bathtub-type electrode. Specifically, electroporation may be performed under the conditions described above. The target organ for gene transfer is not limited similarly as described above, and includes kidney, liver, spleen, heart and lung, but kidney is particularly preferable. The organ may be derived from any desired mammal. However, as non-human organs for transplantation into humans, pig organs are preferable. The pig organs used in the present invention may include those that have been genetically engineered to suppress the immune reaction that results upon transplantation into humans. The method of the present invention for long-term expression accomplishes an expression of the introduced gene for 3 days or longer, preferably 1 week (7 days) or longer, more preferably 2 weeks (14 days) or longer, more preferably 1 month (30 days) or longer, more preferably 2 months (60 days) or longer, and even more preferably 3 months (90 days) or longer. A vector incorporating viral latent infection machinery or a strong expression vector is suitable as the expression vector of the present invention. Specifically, preferable latent infection machineries include those of EB virus, i.e., EBNA-1 gene or oriP sequence, or combination thereof. Preferable strong expression vectors include expression vectors carrying the cytomegalovirus enhancer and chicken β-actin promoter. The gene to be introduced is not limited, but introduction of a gene encoding a protein having organ damage suppressing function enables to suppress tissue damages of an organ for a long term. Therefore, such a method enables to protect the transplanted organs from cytotoxicity and achieves long-term survival following organ transplantation.

The method of gene transfer of the present invention is particularly useful for suppressing organ rejection following transplantation and/or for achieving long-term survival of transplanted organs. By the introduction of a gene encoding a protein having organ damage suppressing function into an injection area through a vascular system or a ureter of a donor organ to be transplanted, organ rejection following transplantation is suppressed and an organ that survives for a long term can be prepared. The transplantation of the prepared organ into a recipient suppresses organ rejection following transplantation that results in long-term survival of the transplanted organ. The method for suppressing graft rejection and attaining long-term survival of the present invention is preferably used for kidney transplantation. Specifically, HGF gene can be mentioned as a gene encoding a protein having organ damage suppressing function. Herein, the term "HGF gene" refers to a gene expressing HGF, and includes genes whose nucleotide sequence is partially deleted, substituted with other bases, inserted with a part of other nucleotide sequence or linked to other bases at the 5'- or 3'-terminus as long as the protein expressed from the gene substantially has an equivalent function to HGF. The "HGF genes" that may be used in the present invention include, for example, those described in Nature, 342:440 (1989), Biochem. Biophys. Res. Commun., 163:967 (1989), etc.

An "HGF gene" drug may be administered by injecting the "HGF gene" drug through the renal artery or ureter after perfusion of kidney with an appropriate perfusion solution (e.g., buffer or physiological saline) through the renal artery or ureter following removal of the kidney to be transplanted. The renal vein may be ligated at the time the "HGF gene" drug is injected. The temperature of the perfusion solution or the "HGF gene" drug may be appropriate temperature between 4° C. and 37° C., but is preferably 37° C. The kidney to be transplanted, injected with the "HGF gene" drug is preferably subjected to gene transfer by electroporation, and then transplanted into a recipient. The conditions for the "electroporation" may be appropriately adjusted according to the age, body weight of the patient. Electrodes used for the electroporation may be a "bathtub-type electrode" filled with an appropriate solvent (e.g., sterilized buffer or physiological saline) or forceps-type electrodes, but the "bathtub-type electrode" is particularly preferred. In the use of the "bathtub-type electrode", the kidney may be covered with an appropriate protector (e.g., sterilized gauze). The gene transfer is preferably performed with a square-shaped voltage for "electroporation", and a voltage of 1 to 200 V, particularly 30 to 100 V for 100 milliseconds is applied six times with intervals of 900 milliseconds. However, these conditions may be appropriately adjusted according to the measurement of the kidney. Preferably, immediately after the gene transfer, the kidney for transplantation is perfused with an appropriate solution (University of Wisconsin (UW) solution, for instance) cooled to 4° C. to transplant the kidney into a recipient.

The content of a "HGF gene" in a drug can be appropriately adjusted according to the age, body weight, etc. of the patient. It is generally, 0.1 mg to 100 mg, however, preferably 10 mg to 30 mg of the HGF gene is suitably administered for kidney transplantation.

The above HGF gene drug comprising a vector encoding HGF as an active ingredient serves as a pharmaceutical composition that may be used for suppressing organ rejection and/or achieving long-term survival of organs following transplantation, such as kidney transplantation. The present invention provides such pharmaceutical compositions and kits comprising the pharmaceutical compositions. In addition to a vector comprising a gene encoding HGF, the kits may contain other vectors comprising other genes having organ damage suppressing function. Specifically, the kit may contain a vector comprising a gene encoding a molecule involved in fibrosis suppression, apoptosis suppression or immunosuppression. Alternatively, the kits may comprise a low molecular weight compound having organ damage suppressing function. Furthermore, the kits may be accompanied with an instruction describing the administration method as above for introducing the vector comprising the gene encoding HGF into organs to be transplanted.

Moreover, the method for gene transfer of the present invention may be further used for introducing a DNA enzyme that counteracts against a protein not preferred in a target organ, for example, proteins that induce fibrosis and such by suppressing cell proliferation in the organ.

BEST MODE FOR CARRYING OUT THE INVENTION

Herein below, the present invention will be specifically described using Examples, however, it is not to be construed as being limited thereto. References cited in the present specification are herein incorporated in their entirety.

EXAMPLE 1

Introduction of FITC-Labeled Oligo DNA into Rat Kidney (1)

Figure 1:
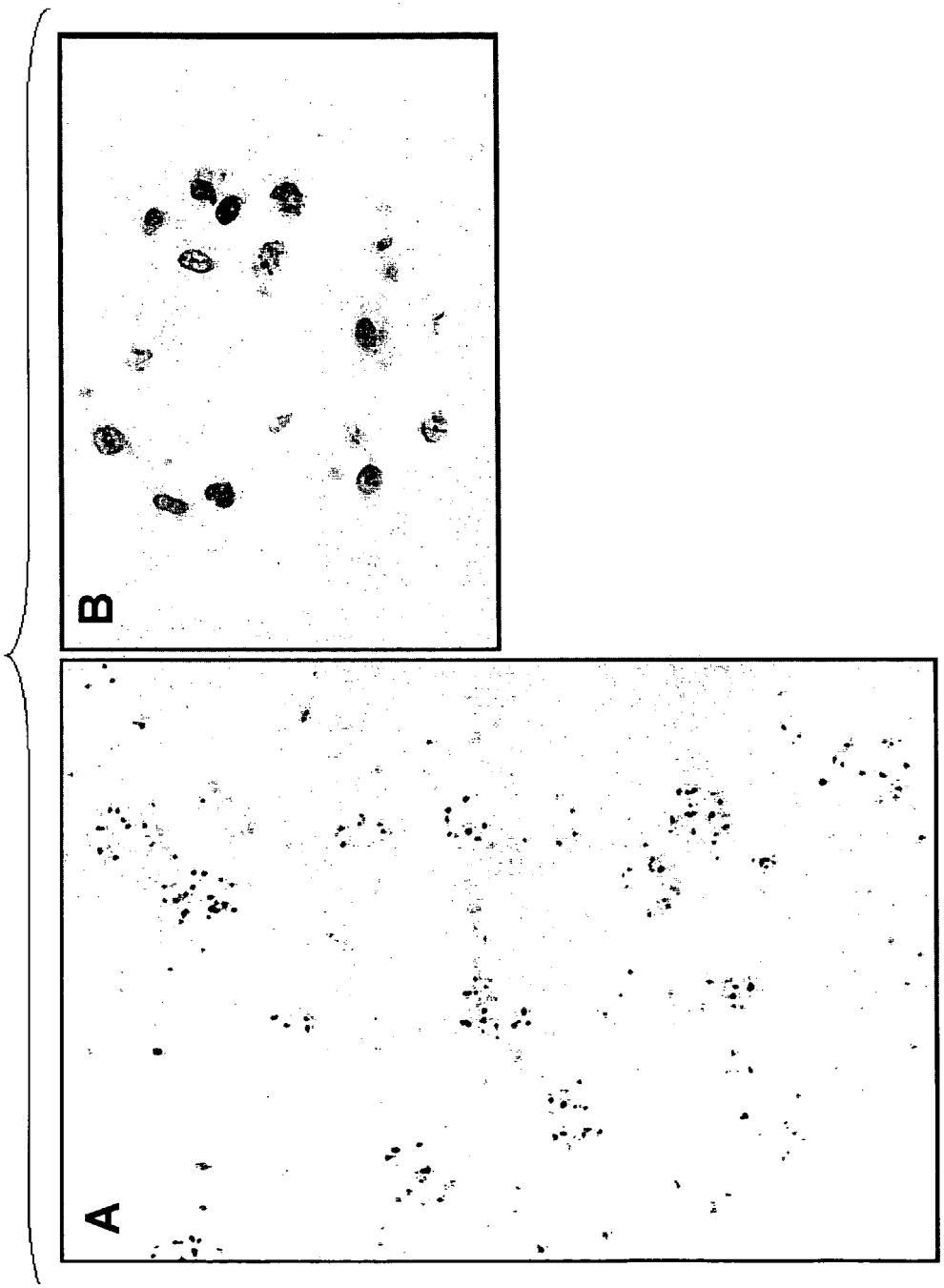
FIG. 1 depicts photographs showing the result of fluorescent microscopy examining the localization of fluorescein isothiocyanate (FITC)-labeled oligo DNA in the kidney injected with the oligo DNA through the rat renal artery and performing gene transfer by electroporation as described in Example 1 (a, ×100; b, ×400).
Figure 2:
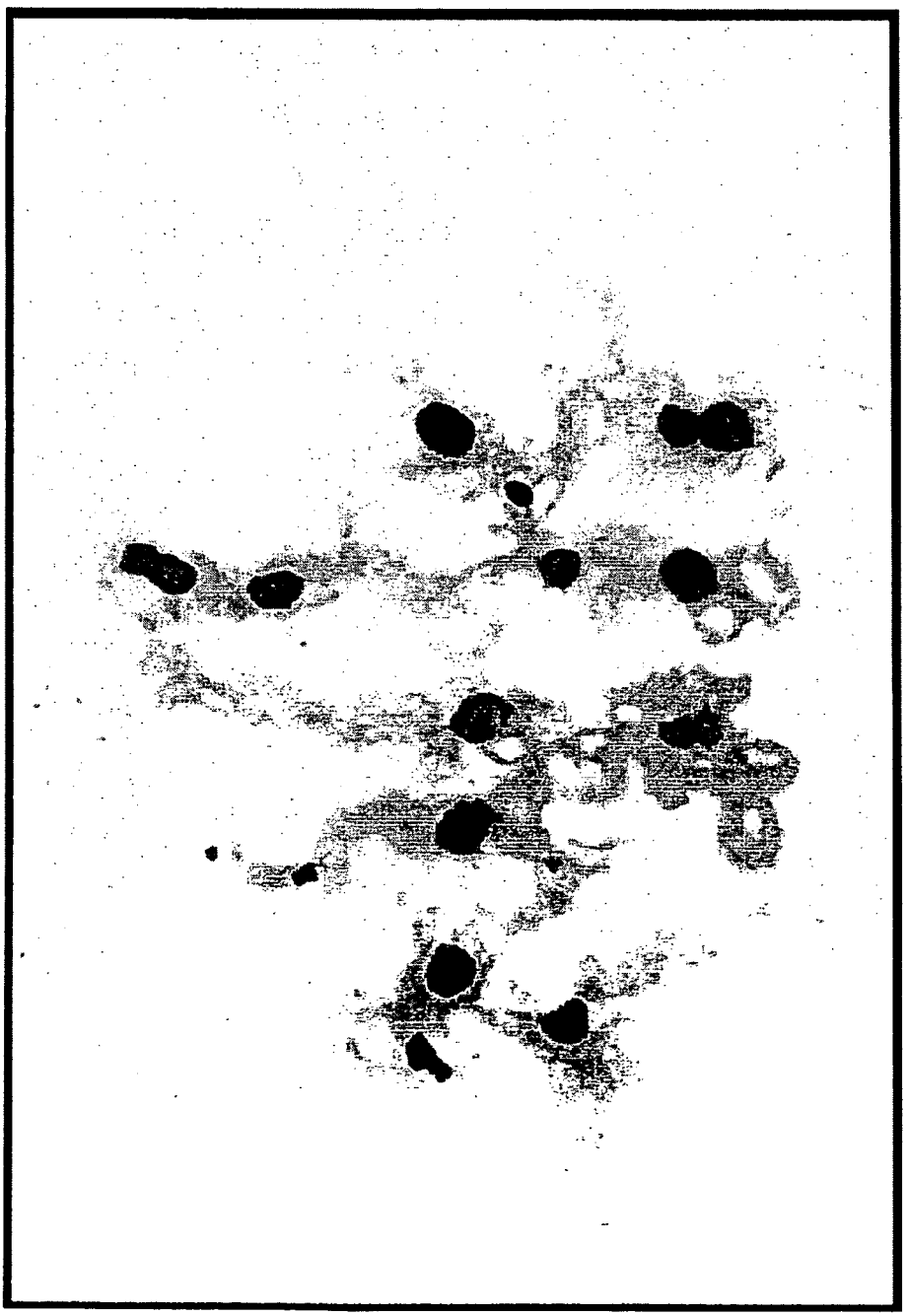
FIG. 2 depicts a photograph showing the result of examination on the localization of oligo DNA introduced into the glomerulus using rhodamine-labeled anti-Thy-1 antibody, an antibody against rat mesangial cells.

A twelve base pair oligo DNA fluorescently labeled with FITC at the 5'-terminus (5'-FITC-CGAGGGCGGCATGGG-3'; SEQ ID NO: 1) was dissolved in buffer (137 mM NaCl, 5.4 mM KCl, 10 mM Tris-HCl [pH 7.6]; hereinafter abbreviated as "BSS") at a concentration of 50 μg/500 μl for gene transfer. Sprague Dawley (hereinafter abbreviated as "SD") rat (6-week-old male) was anesthetized by intraperitoneal administration of pentobarbital (50 mg/kg). After dissection of the abdomen, a kidney was exposed and a 24 G catheter (Terumo Corporation) was inserted into the renal artery for perfusion of the kidney with physiological saline and the oligo DNA described above was injected. Immediately after the injection of the oligo DNA, the renal vein was ligated with a clip. The kidney introduced with the DNA was nipped with the forceps-type electrodes to conduct gene transfer by electroporation applying a square-shaped voltage (75 V, 100 milliseconds) six times with intervals of 900 milliseconds. The catheter was removed after the gene transfer and the puncture was sealed with Aron Alpha® for biomedical use to stop bleeding. Ten minutes after the gene transfer, the kidney was removed and observed under a fluorescent microscope. To confirm the localization of the oligo DNA in the renal glomerulus, the organ was examined using antibody against Thy-1 antigen, a marker for rat mesangial cells. As shown in FIG. 1, the FITC-labeled oligo DNA was introduced in the nuclei of all of the glomerulus and a few of interstitial cells. The oligo DNA was not introduced into the renal tubular cells at all. Moreover, as shown in FIG. 2, upon staining the kidney that was subjected to gene transfer with rhodamine-labeled anti-Thy-1 antibody, the mesangial area was stained red, but the fluorescence of the FITC-labeled oligo DNA turned to yellow. Thus, it was revealed that the oligo DNA was introduced into mesangial cells.

EXAMPLE 2

Introduction of FITC-Labeled Oligo DNA into Rat Kidney (2)

Figure 3:
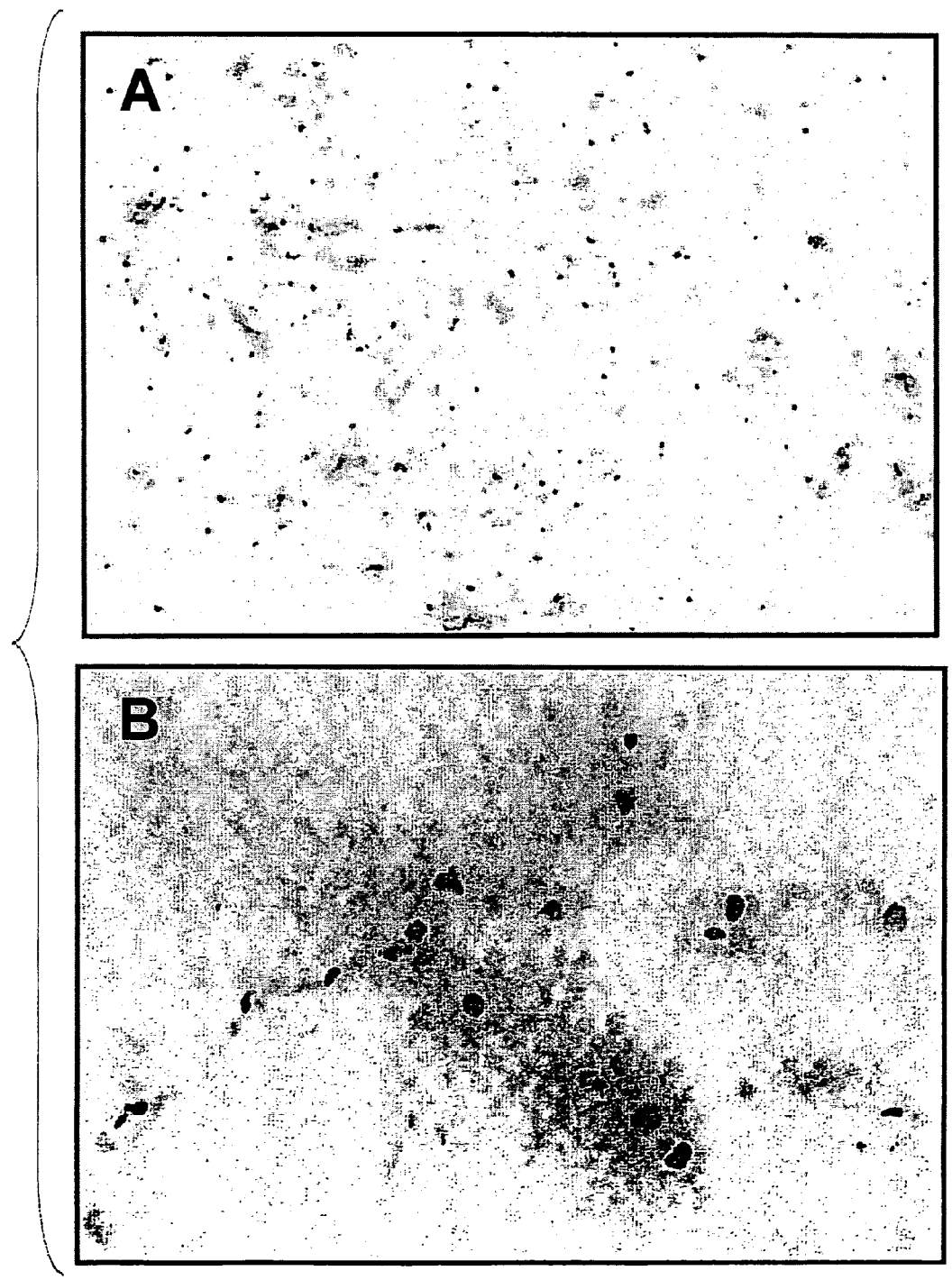
FIG. 3 depicts photographs showing the result of fluorescent microscopy examining the localization of FITC-labeled oligo DNA in the kidney injected with the oligo DNA through the rat ureter and performing gene transfer by electroporation as described in Example 2 (a, ×100; b, ×400).

A twelve base pair oligo DNA fluorescently labeled with FITC at the 5'-terminus (5'-FITC-CGAGGGCGGCATGGG-3'; SEQ ID NO: 1) was dissolved in BSS at a concentration of 50 μg/500 μl for gene transfer. SD rat (6-week-old male) was anesthetized by intraperitoneal administration of pentobarbital (50 mg/kg). After abdominal dissection, the left kidney and left ureter were exposed, a 30 G needle (Terumo Corporation) was inserted into the ureter, and the renal artery and vein were clamped with clips to inject the above-described oligo DNA into the kidney. The kidney introduced with the DNA was nipped with forceps-type electrodes to perform gene transfer by electroporation applying a square-shaped voltage (75 V, 100 milliseconds) six times with intervals of 900 milliseconds. Ten minutes after the gene transfer, the kidney was removed and observed under a fluorescent microscope. As shown in FIG. 3, the FITC-labeled oligo DNA was introduced in the nuclei of interstitial cells.

EXAMPLE 3

Introduction of Luciferase Gene into Rat Kidney (1)

Figure 4:
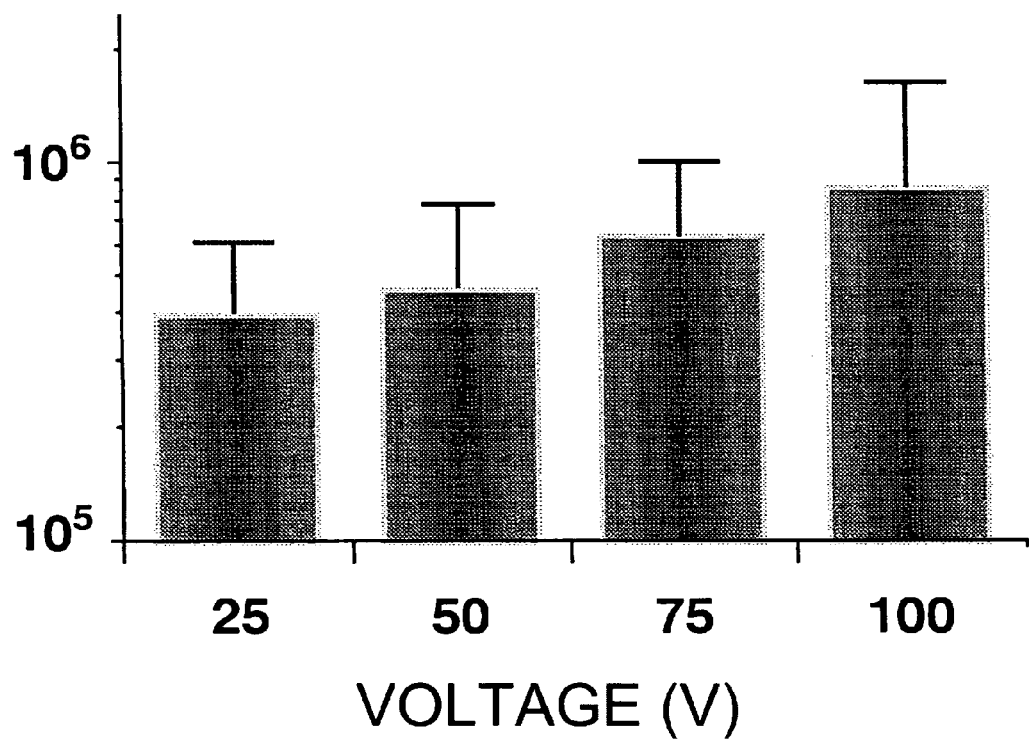
FIG. 4 depicts a graph showing the relationship between the voltage and the expression of the luciferase gene in the renal glomerulus four days after the injection of the luciferase gene through the renal artery and performing gene transfer by electroporation as described in Example 3. While a voltage between 200 V and 1000 V has been used for electroporation in gene transfer into cultured cells, a voltage above 100 V caused organ damage in the gene transfer into kidneys. Thus, a voltage no more than 75 V was indicated to be preferable for gene transfer into kidneys.
Figure 5:
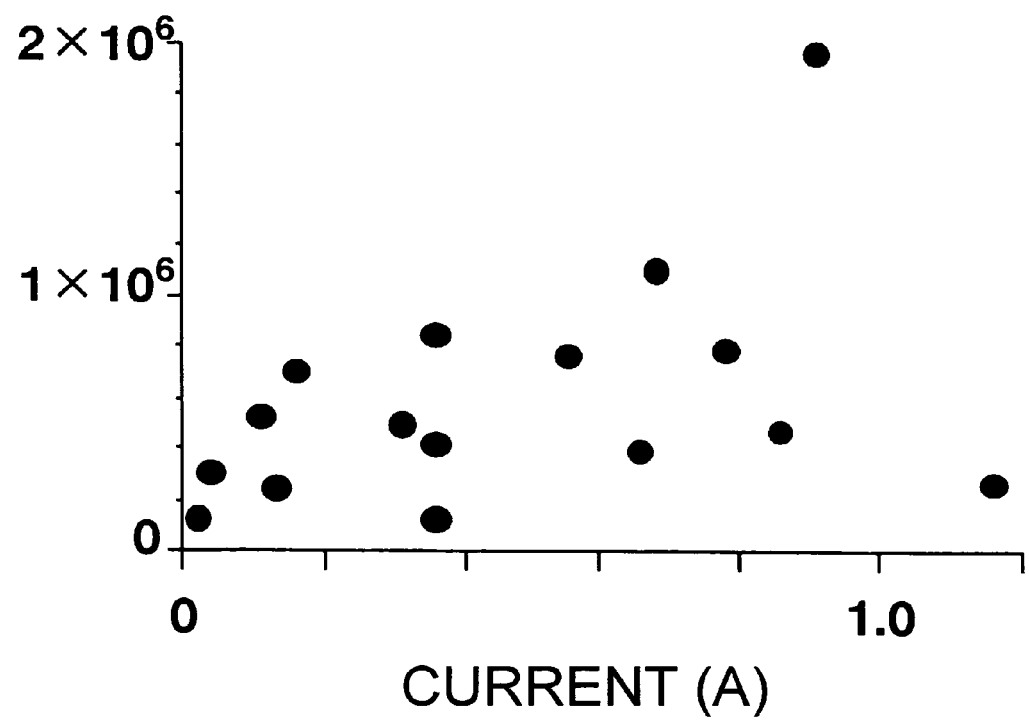
FIG. 5 depicts a graph showing the relationship between the electric current and the expression of the luciferase gene in the renal glomerulus four days after the injection of the luciferase gene through the renal artery and performing gene transfer by electroporation as described in Example 3.

An expression vector carrying a latent infection machinery of EB virus inserted with a luciferase gene was constructed. The expression vector was dissolved in BSS at a concentration of 200 μg/500 μl for gene transfer. SD rats (6-week-old males) were anesthetized by intraperitoneal administration of pentobarbital (50 mg/kg). After abdominal dissection, kidneys were exposed and 24 G catheter was inserted into the renal artery for perfusion of the kidneys with physiological saline and the above-described expression vector was injected. Immediately after the injection of the expression vector, the renal vein was ligated with a clip. The kidneys introduced with the gene were nipped with forceps-type electrodes to perform gene transfer by electroporation applying a square-shaped voltage (25, 50, 75 or 100 V, 100 milliseconds) six times with intervals of 900 milliseconds. The catheter was removed after the gene transfer, and the puncture was sealed with Aron Alpha® for biomedical use to stop bleeding. Four days after the gene transfer, the kidneys were removed, and the renal glomeruli were isolated by the sieving method to measure the luciferase activity in the glomeruli. The protein content in the glomeruli was also measured at the same time to examine the influence of voltage and electric current on the expression level of the gene. The measured protein content was used to correct the luciferase expression level in the glomerul. As shown in FIG. 4, although the luciferase activity tended to increase in accordance with the increase of the voltage between a voltage from 25 V to 100 V, but without significant difference. Furthermore, as shown in FIG. 5, no correlation between the electric current and the gene expression level could be confirmed. Although the renal glomeruli and renal tubular cells showed no histological change, a voltage of 100 V caused burns on the surface of fibrous capsule of kidney. Thus, a voltage of 75 V was used in following analyses.

EXAMPLE 4

Introduction of Luciferase Gene into Rat Kidney (2)

Figure 6:
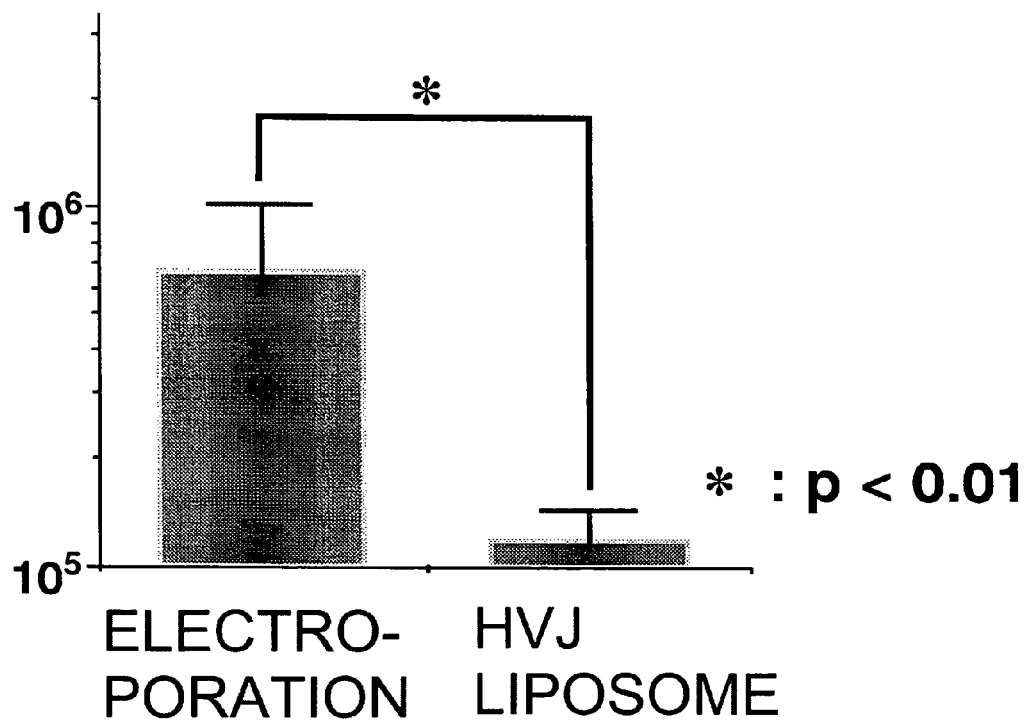
FIG. 6 depicts a graph showing the relationship between the gene transfer methods and the expression of the luciferase gene in the renal glomerulus four days after the injection of the luciferase gene through the renal artery and performing gene transfer by electroporation or the HVJ liposome method as described in Example 4.

An expression vector carrying a latent infection machinery of EB virus inserted with a luciferase gene was constructed. The expression vector was dissolved in BSS at a concentration of 200 µg/500 µl for gene transfer. SD rats (6-week-old males) were anesthetized by intraperitoneal administration of pentobarbital (50 mg/kg). After abdominal dissection, a kidney was exposed, and a 24 G catheter was inserted into the renal artery for perfusion of the kidney with physiological saline. Then, the above-described expression vector was injected into the kidney. Immediately after the injection of the expression vector, the renal vein was ligated with clips. The kidney introduced with the gene was nipped with forceps-type electrodes to perform gene transfer by electroporation applying a square-shaped voltage (75 V, 100 milliseconds) six times with intervals of 900 milliseconds. Alternatively, a liposome solution containing 200 µg of the expression vector enclosed in HVJ-liposomes was prepared, similarly injected through the renal artery and then the kidney was incubated with the gene for 10 minutes. The catheter was removed after the gene transfer and the puncture was sealed with Aron Alpha® for biomedical use to stop bleeding. Four days after the gene transfer, the kidneys were removed and the renal glomeruli were isolated by the sieving method to measure the luciferase activity in the glomeruli. The protein content in the glomeruli was measured at the same time and used to correct the luciferase expression level in the glomeruli to compare the gene transfer efficiency between the electroporation and the HVJ liposome methods. As shown in FIG. 6, the gene transfer efficiency of electroporation was about six times higher than that of the HVJ liposome method.

EXAMPLE 5

Introduction of Luciferase Gene into Rat Kidney (3)

Figure 7:
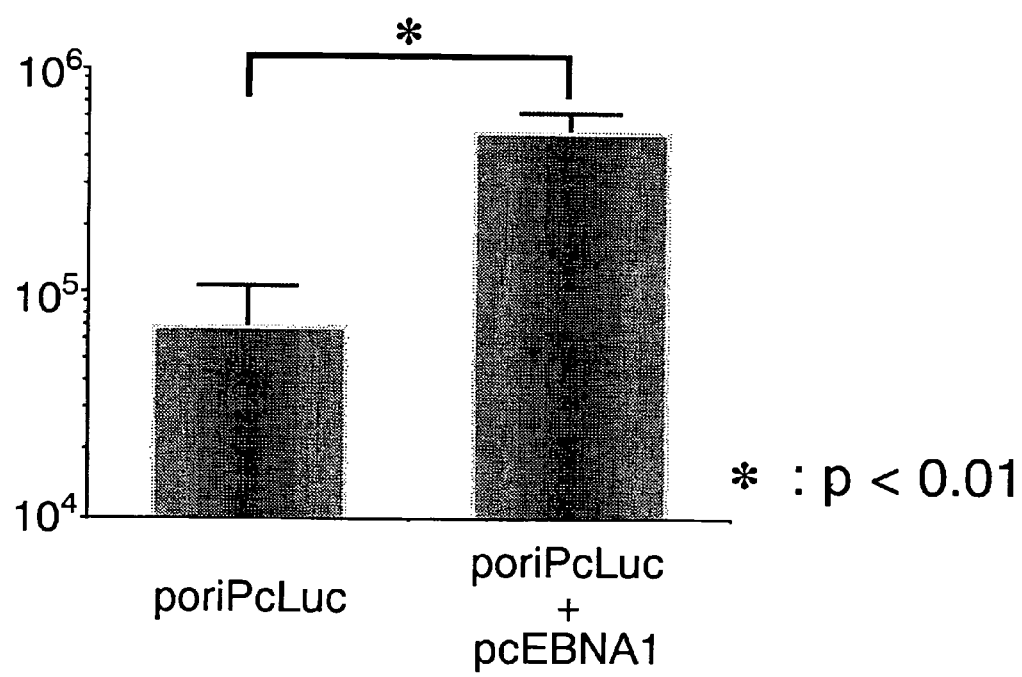
FIG. 7 depicts a graph showing the result of examination on the efficiency of gene transfer using a combination of the luciferase gene and EBNA-1 gene as described in Example 5.

In order to examine whether an effect of combination of transgenes in gene transfer by electroporation can be obtained, an expression vector carrying a luciferase gene downstream to the oriP sequence, one of the latent infection machineries of EB virus, (poriP-cLuc) and an expression vector carrying the other latent infection machinery, the EBNA-1 gene (pcEBNA) were constructed. A DNA solution wherein 163 µg of poriP-cLuc and 121 µg of pcEBNA were dissolved in 500 µl of BSS and a DNA solution wherein 163 µg of poriP-cLuc was dissolved in 500 µl of BSS were prepared for gene transfer. SD rats (6-week-old males) were anesthetized by intraperitoneal administration of pentobarbital (50 mg/kg). After abdominal section, kidneys were exposed and a 24 G catheter was inserted into the renal artery for perfusion of the kidneys with physiological saline and the above-described expression vectors were injected. Immediately after the injections of the expression vectors, the renal veins were ligated with clips. The kidneys introduced with the genes was nipped with forceps-type electrodes to perform gene transfer by electroporation applying a square-shaped voltage (75 V, 100 milliseconds) six times with intervals of 900 milliseconds. The catheter was removed after the gene transfer and the puncture was sealed with Aron Alpha® for biomedical use to stop bleeding. Four days after the gene transfer, the kidneys were removed and the renal glomeruli were isolated by the sieving method to measure the luciferase activity in the glomeruli. The protein content in the glomeruli was measured at the same time, and used to correct the luciferase expression level in the glomeruli to examine the effect of the combination of transgenes. As shown in FIG. 7, the combination of poriP-cLuc gene and pcEBNA gene was revealed to show a gene expression level about seven-fold higher than that obtained with poriP-cLuc gene alone.

EXAMPLE 6

Introduction of Luciferase Gene into Rat Kidney (4)

Figure 8:
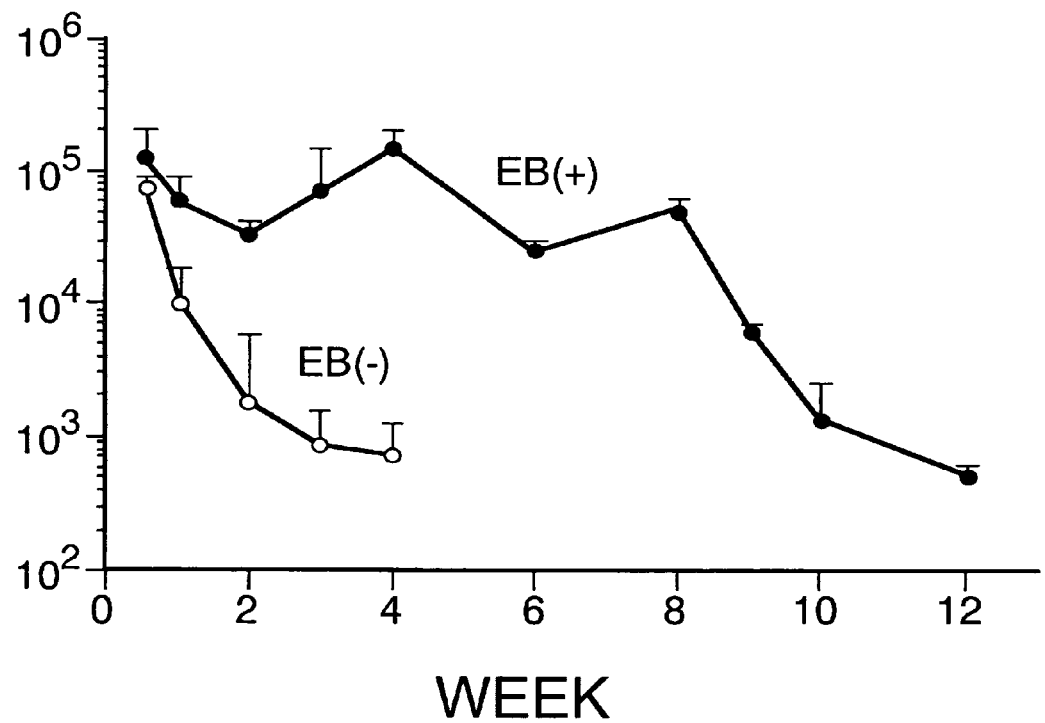
FIG. 8 depicts a graph showing the result of examination on the duration of gene expression using the expression vector carrying the oriP sequence and EBNA-1 gene, latent infection machineries of Epstein-Barr (EB) virus, as described in Example 6.

An expression vector carrying a latent infection machinery of EB virus inserted with a luciferase gene and a luciferase expression vector without the machinery were constructed. The vectors were dissolved in BSS at a concentration of 200 µg/500 µl for gene transfer. SD rats (6-week-old males) were purchased from SLC Inc. and gene transfer was performed by the method described above. The catheter was removed after the gene transfer, and the puncture was sealed with Aron Alpha® for biomedical use to stop bleeding. The kidneys were removed 4, 7, 14, 21, 28, 42, 56, 63, 70 and 84 days after the gene transfer and the renal glomeruli were isolated by the sieving method to measure the luciferase activity in the glomeruli. The protein content in the glomerulus was measured at the same time, and used to correct the luciferase expression level in the glomeruli to examine the duration of gene expression. As shown in FIG. 8, the luciferase gene expression levels were similar at four days after the gene transfer regardless of the presence of the latent infection machinery of EB virus. However, the expression level decreased after 1 week from the gene transfer in the glomeruli introduced with the expression vector without the viral latent infection machinery and almost no expression could be detected after 4 weeks. In contrast, the expression level in the glomeruli introduced with the expression vector carrying the latent infection machinery of EB virus was maintained after 8 weeks at a similar level to that detected after 4 days, and the expression was preserved until the tenth weeks.

EXAMPLE 7

Introduction of FITC-Labeled Oligo DNA into Pig Kidney

A twelve base pair oligo DNA labeled with FITC at the 5'-terminus (5'-FITC-CGAGGGCGGCATGGG-3'; SEQ ID NO: 1) was dissolved in BSS at a concentration of 3 mg/50 ml for gene transfer. After abdominal section of a miniature pig under anesthetization, a kidney was removed, perfused with saline and the above-described oligo DNA was injected. After injection of 25 ml of the oligo DNA, the renal vein was ligated with clips, and another 25 ml of the oligo DNA was injected. The pig kidney introduced with the DNA was immersed in a bathtub-type electrode filled with physiological saline (FIG.

Figure 9:
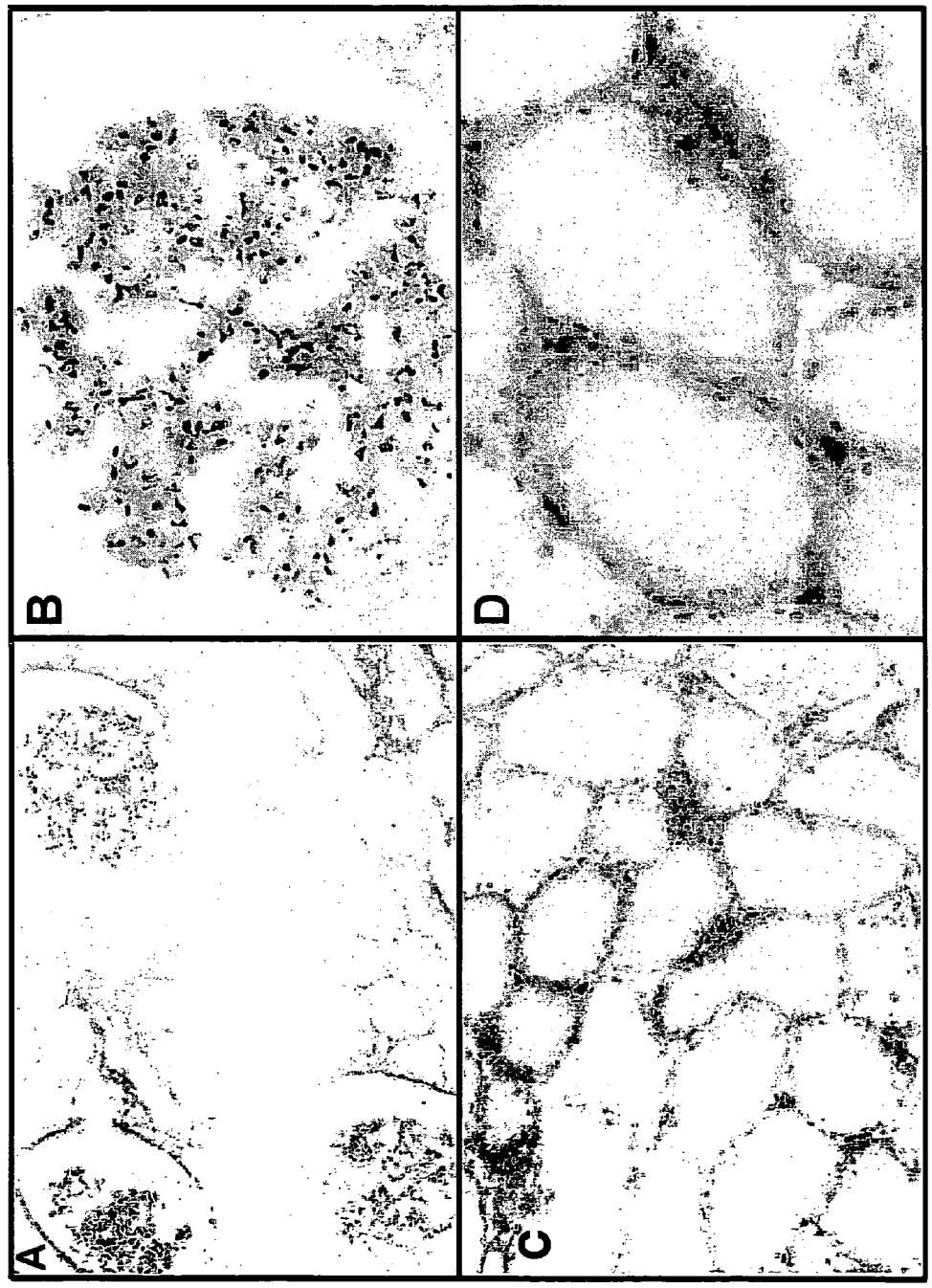
FIG. 9 depicts photographs showing the result of fluorescent microscopy examining the localization of FITC-labeled oligo DNA in pig kidney by injecting the oligo DNA through the renal artery and performing gene transfer by electroporation as described in Example 7. A voltage of 30 to 50 V was appropriate for the gene transfer using a bathtub-type electrode. (a and c, ×100; b and d, ×400; a and b, the glomerulus-centered image; c and d, the interstitium-centered image).
Figure 11:
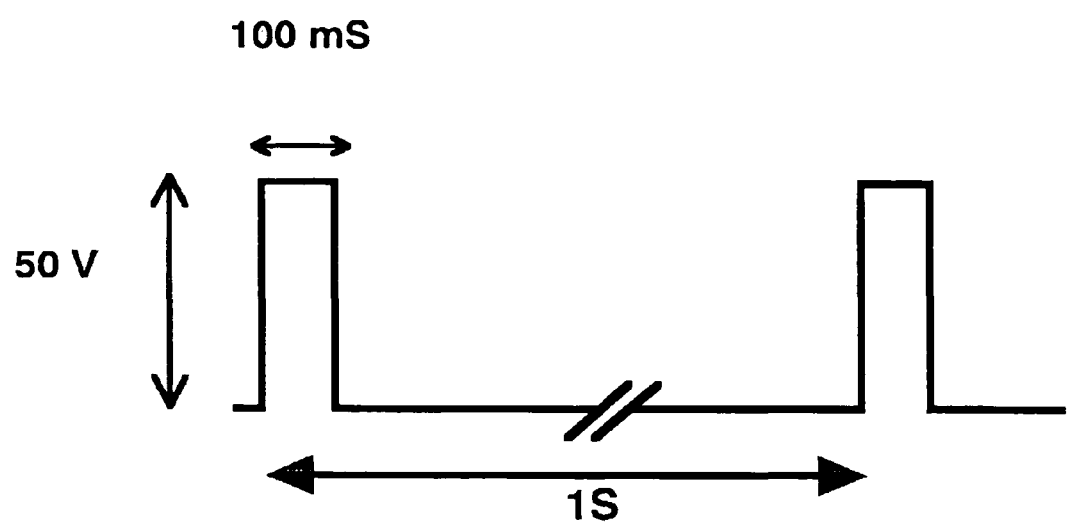
FIG. 11 depicts a diagram showing an example of rectangle waves of voltage used for electroporation on pig kidneys.

10) to perform gene transfer by electroporation applying a square-shaped voltage (30 V, 100 milliseconds) six times with intervals of 900 milliseconds (FIG. 11). After the gene transfer, the kidney was perfused with physiological saline and observed under a fluorescent microscope. As shown in FIG. 9, the FITC-labeled oligo DNA was introduced in the nuclei of the glomeruli and interstitial cells.

EXAMPLE 8

Introduction of FITC-Labeled Oligo DNA into Pig Kidney Through the Ureter

Figure 10:
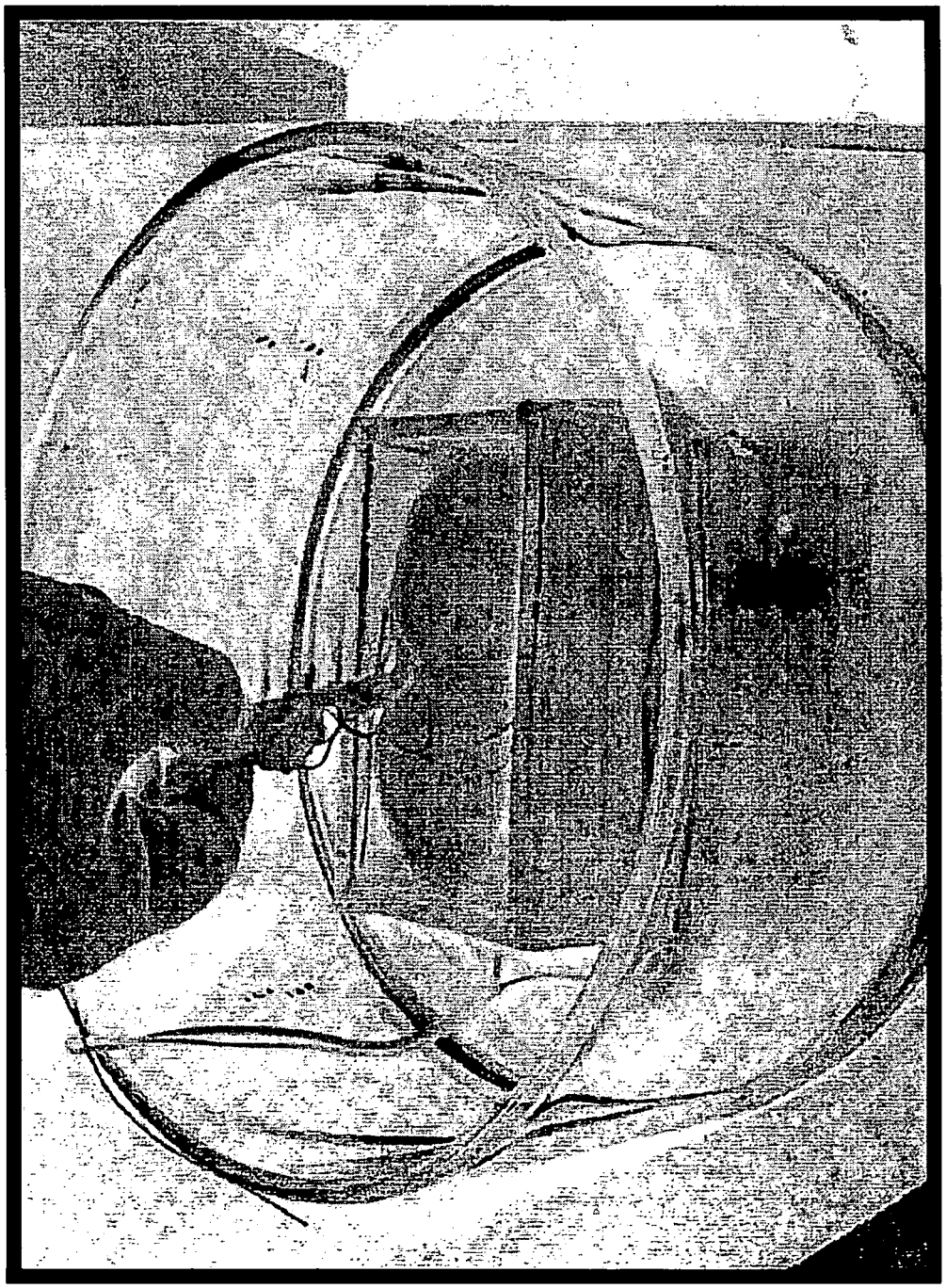
FIG. 10 depicts a photograph showing the electrode used for electroporation on pig kidneys. Stainless steel electrodes were placed on both sides of the bathtub.
Figure 12:
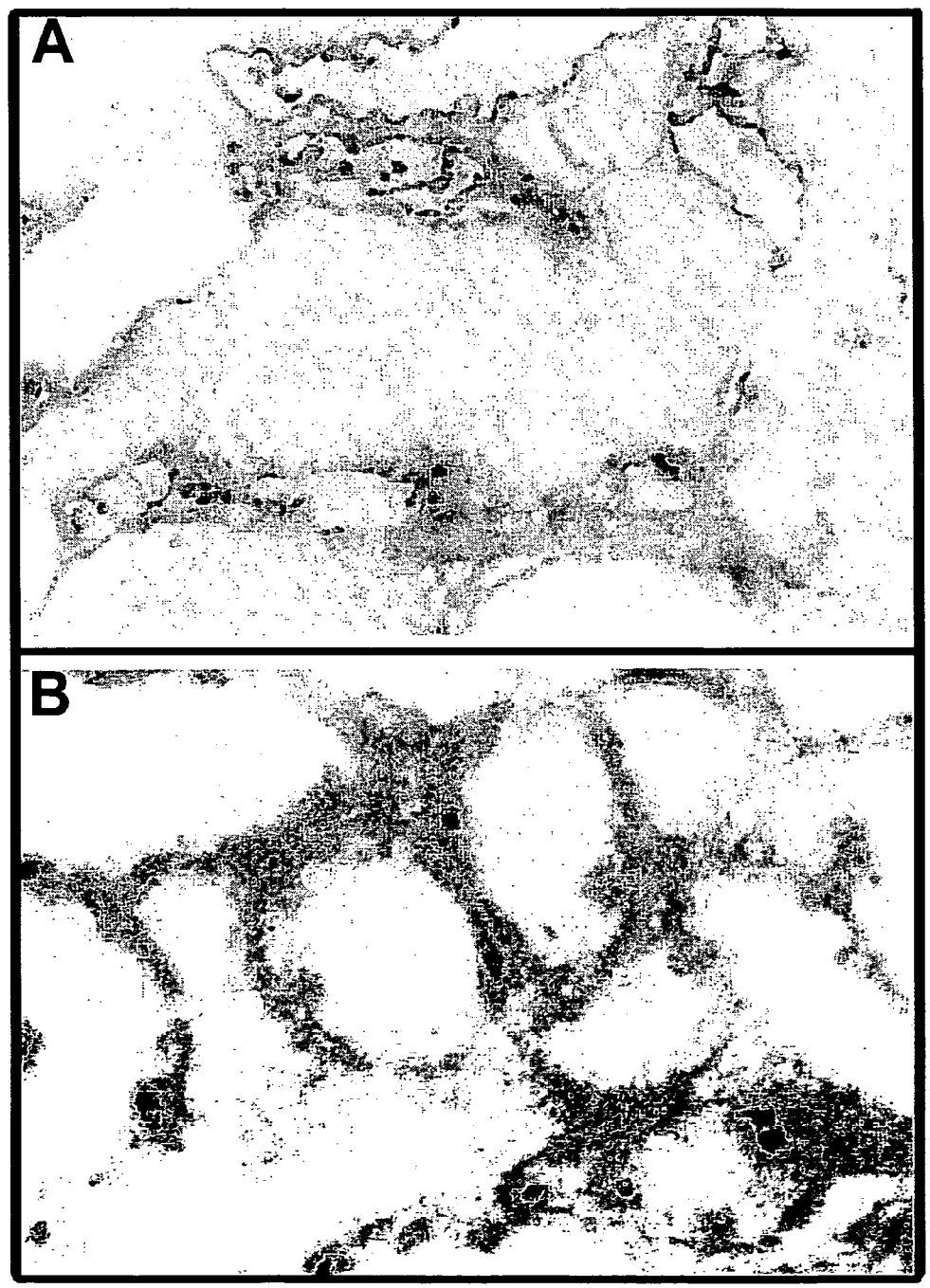
FIG. 12 depicts photographs showing the result of fluorescent microscopy examining the localization of FITC-labeled oligo DNA in pig kidney by injecting the oligo DNA through the ureter and performing gene transfer by electroporation as described in Example 8 (a, ×100; b, ×400).

A twelve base pair oligo DNA labeled with FITC at the 5'-terminus (5'-FITC-CGAGGGCGGCATGGG-3'; SEQ ID NO: 1) was dissolved in BSS at a concentration of 3 mg/50 ml for gene transfer. After abdominal section of a miniature pig under anesthetization, a kidney was removed, perfused with saline, and the above-described oligo DNA was injected through the ureter. After the injection of 25 ml of the oligo DNA, the renal vein was ligated with clips, and another 25 ml of the oligo DNA was injected. The pig kidney introduced with the DNA was immersed in a bathtub-type electrode filled with physiological saline (FIG. 10) to perform gene transfer by electroporation applying a square-shaped voltage (30 V, 100 milliseconds) six times with intervals of 900 milliseconds (FIG. 11). After the gene transfer, the kidney was perfused with physiological saline and observed under a fluorescent microscope. As shown in FIG. 12, the FITC-labeled oligo DNA was introduced in the nuclei of interstitial cells.

EXAMPLE 9

Introduction of Luciferase Gene into Pig Kidney

Figure 13:
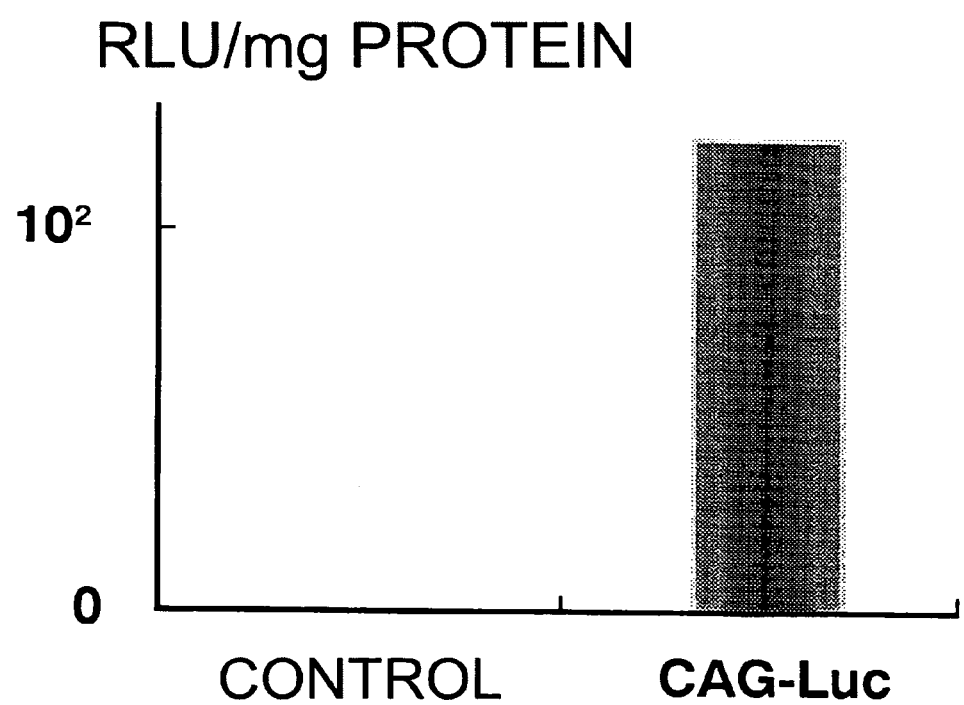
FIG. 13 depicts a graph showing the result of examination on the expression of the luciferase gene in the pig renal cortex removed four days after the injection of the luciferase gene through the renal artery, performing gene transfer by electroporation and transplanting the kidney as described in Example 9. Results of the samples introduced with the expression vectors carrying a luciferase gene (CAG-Luc) and a β-galactosidase gene (control) are shown.

An expression vector carrying a latent infection machinery of EB virus inserted with a luciferase gene was constructed. The vector was dissolved in BSS at a concentration of 24 mg/50 ml for gene transfer. After abdominal section of a miniature pig under anesthetization, a kidney was removed, perfused with physiological saline and the above-described expression vector was injected. After the injection of 25 ml of the expression vector, the renal vein was ligated with clips, and another 25 ml of the oligo DNA was injected. The pig kidney introduced with the gene was immersed in a bathtub-type electrode filled with physiological saline to perform gene transfer by electroporation applying a square-shaped voltage (30 V, 100 milliseconds) six times with intervals of 900 milliseconds. The pig kidney subjected to the gene transfer was transplanted and then removed four days after the gene transfer to measure the luciferase activity in the renal cortex. The protein content of the renal cortex was measured at the same time, and used to correct the luciferase expression level in the renal cortex to examine the presence of gene expression. As shown in FIG. 13, the gene was expressed in the pig renal cortex.

EXAMPLE 10

Suppression of Progress of Renal Interstitial Damages by Egr-1 DNA Enzyme Introduction Early growth response factor-1 (Egr-1) regulates the transcription of many cytokines involved in cell proliferation and is associated with progression of renal interstitial fibrosis. Introduction of a DNA enzyme against Egr-1 into interstitial cells using electroporation (EP) was examined for its ability to suppress progress of renal interstitial damages.

A DNA enzyme against rat Egr-1 mRNA (ED5) was prepared and examined whether it suppresses the expression of Egr-1 in normal rat kidney (NRK) cells. Furthermore, using a rat unilateral ureteral obstruction (UUO) model, ED5 and scrambled DNA (SCR) were introduced into renal interstitial cells through the ureter by electroporation to histologically examine the mRNA expression of Egr-1 and αSMA.

As a result, ED5 inhibited Egr-1 expression due to serum stimulation in NRK cells. Introduction of fluorescently labeled oligo DNA through the ureter by electroporation confirmed the introduction of the oligo DNA into interstitial fibroblasts. In rat UUO models, strong expression of Egr-1 and αSMA mRNAs in the interstitium was detected in disease control (DC) group. On the other hand, in the SCR-introduced group the expression was suppressed with the introduction of ED5. Masson's trichrome staining revealed that the interstitial fibrosis detected in the DC-and SCR-introduced groups was suppressed due to the introduction of ED5. Thus, the progress of renal interstitial damages was indicated to be suppressed by introducing a DNA enzyme, such as ED5, into renal interstitial cells by electroporation.

EXAMPLE 11

Introduction of HGF Gene into Pig Kidney

Figure 14:
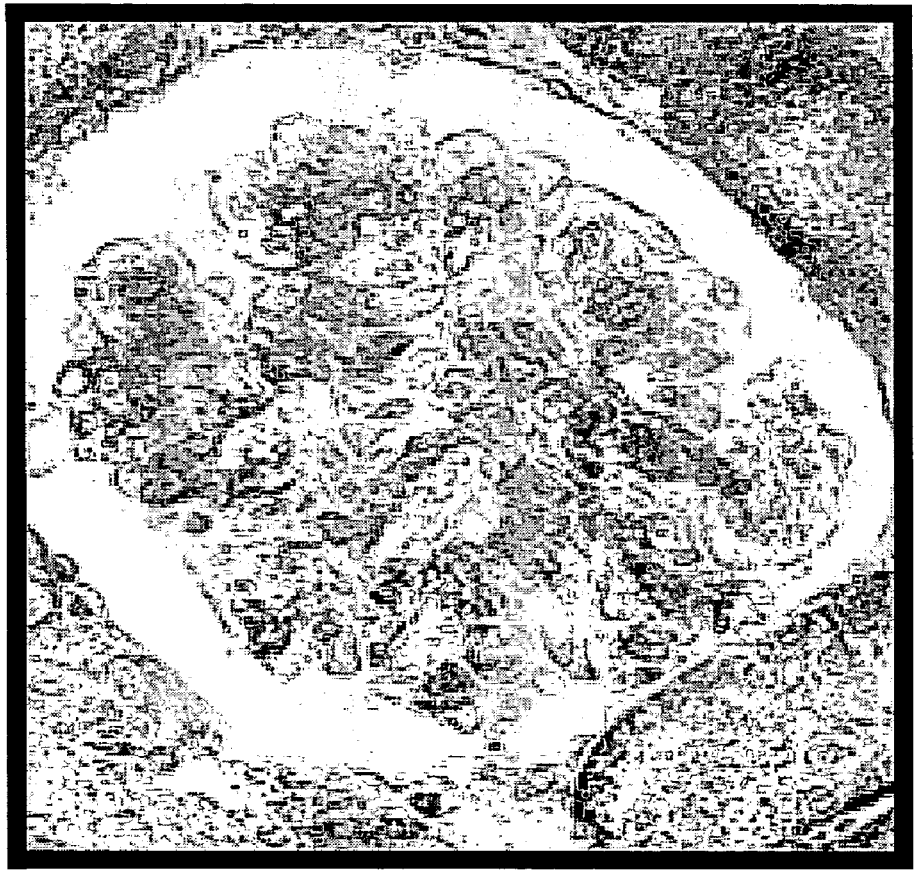
FIG. 14 depicts a photograph confirming HGF expression by enzyme-linked immunoassay one week after the introduction of the HGF gene. The HGF expression was detected in the glomerulus.
Figure 15:
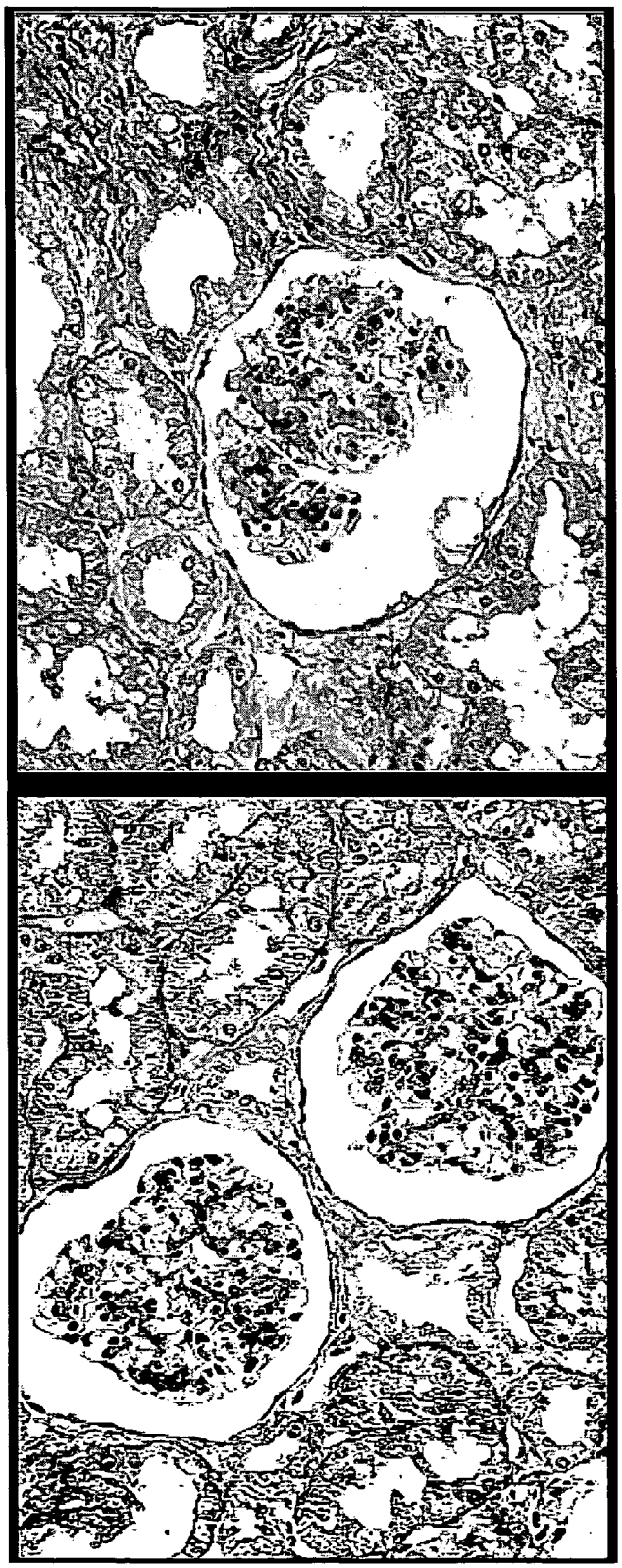
FIG. 15 depicts photographs of the kidney tissues stained by Masson's trichrome staining six months after the introduction of the HGF gene or a β-galactosidase gene as the control. Interstitial fibrosis was observed in the control group, but was suppressed in the group introduced with the HGF gene.
Figure 16:
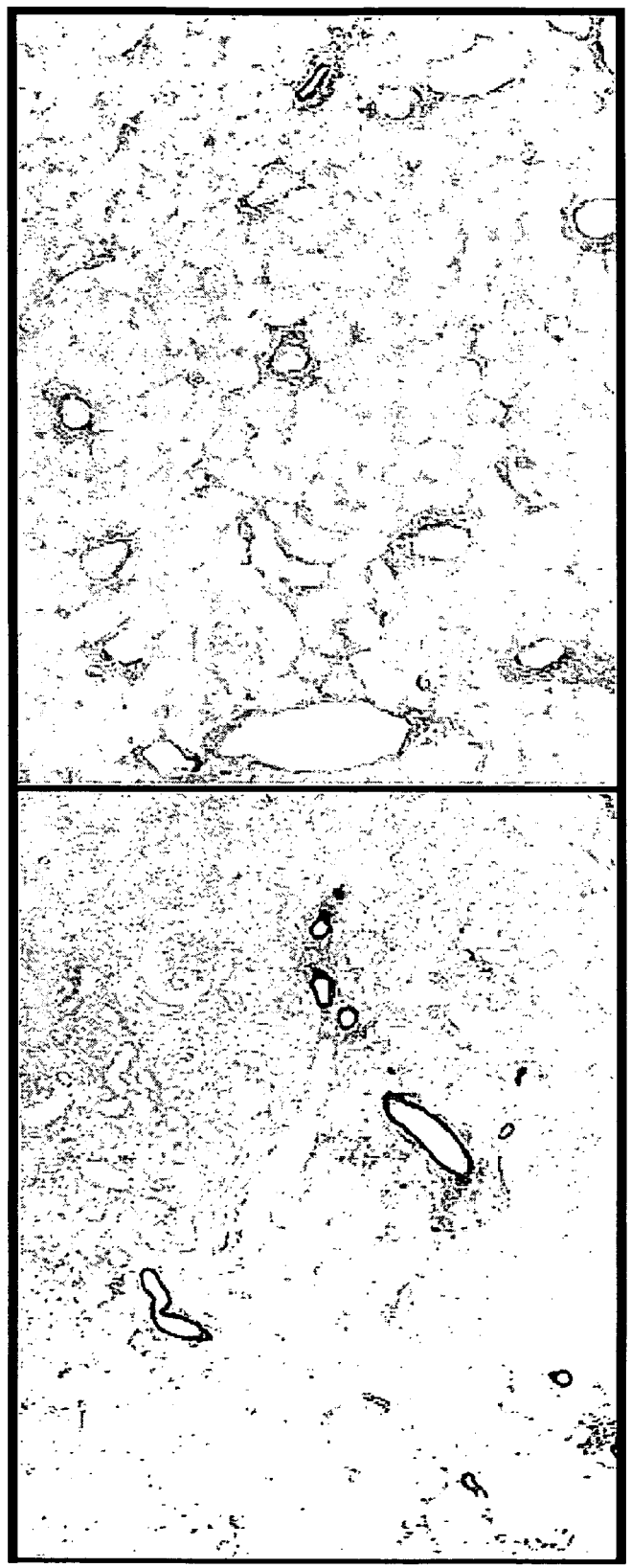
FIG. 16 depicts photographs of the kidney tissues stained for αSMA expression by enzyme-linked immunoassay six months after the introduction of the HGF gene or a β-galactosidase gene as the control. The αSMA expression was detected in the interstitium of the control group, but was suppressed in the group introduced with the HGF gene.
Figure 17:
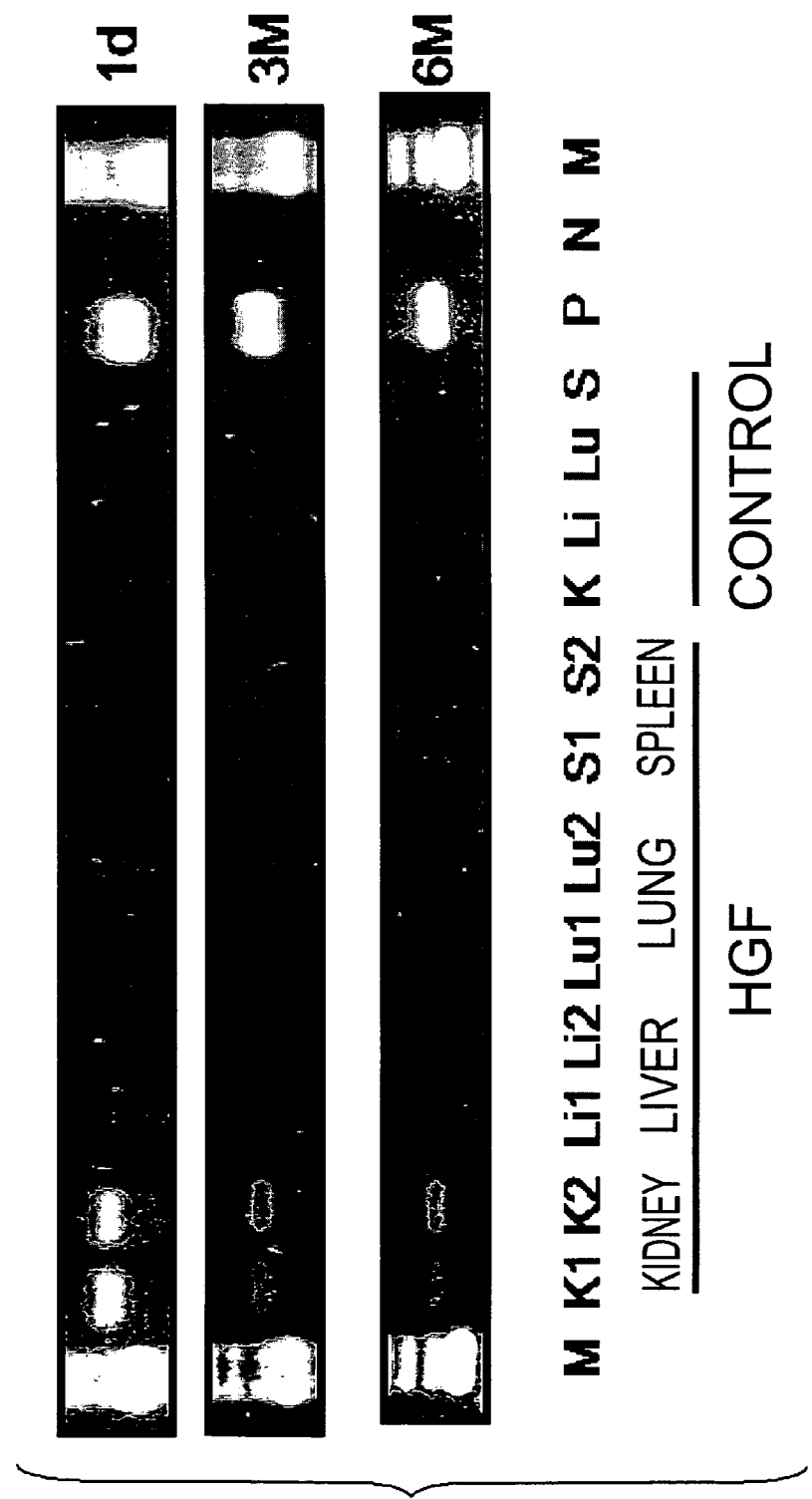
FIG. 17 depicts photographs showing the result of PCR confirming the existence of the HGF gene in the kidney, liver, lung and spleen by recovering the organs one day (1d), and 3 and 6 months (3M and 6M, respectively) after transplantation. The HGF gene was confirmed only in the pig kidney that was introduced with the HGF gene. The gene in the pig kidney could be confirmed even 6 months after the transplantation, but the gene could not be detected in the other organs, i.e., the liver, lung and spleen (K, kidney; Li, liver; Lu, lung; S, spleen).

A strong expression vector wherein a HGF gene is integrated downstream of the cytomegalovirus enhancer and chicken β-actin promoter was constructed. The vector was dissolved in BSS at a concentration of 24 mg/50 ml for gene transfer. After abdominal section of miniature pigs under anesthetization, kidneys were removed, perfused with saline, and the above-described expression vector was injected. After the injection of 25 ml of the expression vector, the renal vein was ligated with clips, and another 25 ml of the oligo DNA was injected. The pig kidneys introduced with the gene were immersed in bathtub-type electrode filled with physiological saline to perform gene transfer by electroporation applying a square-shaped voltage (30 V, 100 milliseconds) six times with intervals of 900 milliseconds. The pig kidneys subjected to gene transfer were transplanted, and the other kidney of the acceptors was removed. First, the presence of HGF gene expression was examined in the transplanted kidney that was removed seven days after the gene transfer. As shown in FIG. 14, HGF gene expression was detected in renal glomeruli of the pig renal cortex. Next, in order to examine the protecting effect of HGF gene transfer on the transplanted kidneys, transplanted kidneys were removed 1, 3 and 6 months after the transplantation for histological analysis. As shown in FIG. 15, interstitial fibrosis was observed in control group introduced with β-galactosidase gene, but was suppressed in the group introduced with the HGF gene. Moreover, as shown in FIG. 16, staining for α smooth muscle actin (αSMA), a marker for the transformation of interstitium, revealed αSMA expression in the interstitium of the control group introduced with the β-galactosidase gene, which expression was suppressed in the group introduced with the HGF gene. Furthermore, the kidney, liver, lung and spleen were removed 1 day, 3 months and 6 months after the transplantation. The existence of the HGF gene in each of the organs was examined by PCR. The HGF gene was detected until the 6 months after the transplantation in only the kidney of the pig introduced with the HGF gene. However, the HGF gene was not detected in the other organs, i.e., liver, lung and spleen (FIG. 17). Furthermore, no HGF gene was detected in the control group.

Thus, the introduction of the HGF gene by electroporation resulted in the expression of the gene in the transplanted kidney alone, and no expression could be detected in the other organs. In addition, the results suggest that the introduction of an HGF gene exhibits a protecting effect on transplanted kidneys.

Industrial Applicability

The method of gene transfer into a kidney to be transplanted via electroporation of the present invention provides a prolonged therapeutic effect as compared to the administration of a HGF protein. Furthermore, the method is safer because HGF can be reacted to the transplanted kidney alone, thereby reducing adverse effects caused by systemic administration of HGF. In addition, the gene transfer method according to the present invention can be used for introducing a DNA enzyme against a protein not preferred in a target organ. For example, proteins inducing fibrosis via the suppression of cell proliferation in the organ can be introduced according to the present method. The method of the present invention may be also useful as an effective method in future xenogeneic transplantation from pigs to humans.

The invention claimed is:

1. A method for introducing a nucleic acid into a kidney, said method comprising the steps of
   (a) injecting an aqueous solution containing a nucleic acid into a renal artery, a renal vein, or a ureter of a kidney;
   (b) setting the whole kidney between forceps-type electrodes; and
   (c) applying electric stimulation at a voltage within the range of 20V to 75V to the whole kidney, thereby introducing the nucleic acid into the kidney.

2. The method according to claim 1, wherein the method results in introduction of the nucleic acid into an area of the kidney in proximity to a blood vessel, interstitial area or area surrounding epithelial cells of the kidney.

3. The method according to claim 1, wherein the method results in introduction of the nucleic acid into an area of the kidney comprising vascular endothelial cells, vascular smooth muscle cells and/or interstitial cells.

4. The method of claim 1, wherein the aqueous solution containing the nucleic acid is injected into a renal artery of the kidney.

5. The method of claim 1, wherein the aqueous solution containing the nucleic acid is injected into a ureter of the kidney.

6. The method of claim 1, wherein the aqueous solution containing the nucleic acid is injected into a renal vein of the kidney.

7. The method of claim 1, wherein step (c) is carried out in vivo.

8. The method of claim 1, wherein step (c) is carried out ex vivo.

9. The method of claim 1, wherein the nucleic acid encodes hepatocyte growth factor.

10. The method of claim 1, wherein the nucleic acid comprises a ribozyme, an antisense nucleic acid, or a DNA enzyme.

11. The method of claim 1, wherein the kidney is a human kidney.

12. The method of claim 1, wherein the kidney is a non-human kidney.

13. The method of claim 12, wherein the non-human kidney is a porcine kidney.

14. The method of claim 1, wherein the voltage is within the range of 40V to 75V.

15. The method of claim 14, wherein the voltage is within the range of 60V to 75V.

16. The method of claim 1, wherein the voltage is a square-shaped voltage.

17. The method of claim 1, wherein the voltage is applied multiple times for 100 milliseconds per time with intervals of 900 milliseconds.

18. The method of claim 1, wherein the kidney is suitable for transplantation.

19. The method of claim 1, wherein the method is used in gene therapy.

20. A method for introducing a nucleic acid into a kidney, said method comprising the steps of
   (a) injecting an aqueous solution containing a nucleic acid into a renal artery, a renal vein, or a ureter of a kidney;
   (b) setting the whole kidney between bathtub-type electrodes ex vivo; and
   (c) applying electric stimulation at a voltage up to 50V to the whole kidney, thereby introducing the nucleic acid into the kidney.

21. The method according to claim 20, wherein the method results in introduction of the nucleic acid into an area of the kidney in proximity to a blood vessel, interstitial area or area surrounding epithelial cells of the kidney.

22. The method according to claim 20, wherein the method results in introduction of the nucleic acid into an area of the kidney comprising vascular endothelial cells, vascular smooth muscle cells and/or interstitial cells.

23. The method of claim 20, wherein the aqueous solution containing the nucleic acid is injected into the renal artery of the kidney.

24. The method of claim 20, wherein the aqueous solution containing the nucleic acid is injected into the ureter of the kidney.

25. The method of claim 20, wherein the aqueous solution containing the nucleic acid is injected into the renal vein of the kidney.

26. The method of claim 20, wherein the nucleic acid encodes hepatocyte growth factor.

27. The method of claim 20, wherein the nucleic acid comprises a ribozyme, an antisense nucleic acid, or a DNA enzyme.

28. The method of claim 20, wherein the kidney is a human kidney.

29. The method of claim 20, wherein the kidney is a non-human kidney.

30. The method of claim 29, wherein the non-human kidney is a porcine kidney.

31. The method of claim 20, wherein step (c) comprises applying a voltage that is within the range of 1V to 50V.

32. The method of claim 31, wherein the voltage is within the range of 30V to 50V.

33. The method of claim 20, wherein the voltage is a square-shaped voltage.

34. The method of claim 20, wherein the voltage is applied multiple times for 100 milliseconds per time with intervals of 900 milliseconds.

35. The method of claim 20, wherein the kidney is suitable for transplantation.

36. The method of claim 20, wherein the method is used in gene therapy.

37. The method of claim 1, wherein the nucleic acid is introduced into a glomerulus of the kidney.

38. The method of claim 1, wherein the nucleic acid is introduced into interstitial cells of the kidney.

39. The method of claim 1, wherein the nucleic acid is introduced into mesangial cells.

40. The method of claim 20, wherein the nucleic acid is introduced into a glomerulus of the kidney.

41. The method of claim 20, wherein the nucleic acid is introduced into interstitial cells of the kidney.

42. The method of claim 20, wherein the nucleic acid is introduced into mesangial cells.

* * * * *

SEQUENCE LISTING

```
<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence:
      artificially synthesized sequence

<400> SEQUENCE: 1
cgagggcggc atggg                                                    15
```